US012796914B2

(12) United States Patent
Preciado et al.

(10) Patent No.: US 12,796,914 B2
(45) Date of Patent: Nov. 17, 2026

(54) IMAGING TARGET MOVEMENT COMPENSATION IN A FOURIER-DOMAIN OPTICAL COHERENCE TOMOGRAPHY IMAGING SYSTEM

(71) Applicant: Optos plc, Dunfermline (GB)

(72) Inventors: Miguel Angel Preciado, Dunfermline (GB); Ewan Rycroft, Dunfermline (GB)

(73) Assignee: Optos plc, Dunfermline (GB)

(*) Notice: Subject to any disclaimer, the term of this patent is extended or adjusted under 35 U.S.C. 154(b) by 156 days.

(21) Appl. No.: 18/527,980

(22) Filed: Dec. 4, 2023

(65) Prior Publication Data

US 2024/0197171 A1 Jun. 20, 2024

(30) Foreign Application Priority Data

Dec. 16, 2022 (EP) .................................... 22214175

(51) Int. Cl.
*A61B 3/10* (2006.01)
*G01B 9/02* (2022.01)
(Continued)

(52) U.S. Cl.
CPC .......... *A61B 3/102* (2013.01); *G01B 9/02043* (2013.01); *G01B 9/02077* (2013.01); *G01B 9/02091* (2013.01); *G16H 40/63* (2018.01)

(58) Field of Classification Search
CPC .... A61B 3/102; A61B 3/154; G01B 9/02091; G01B 9/02062; G01B 9/02063;
(Continued)

(56) References Cited

U.S. PATENT DOCUMENTS

| | | | | |
|---|---|---|---|---|
| 9,763,570 B2 * | 9/2017 | Fingler | .................... | A61B 3/10 |
| 2006/0164653 A1 | 7/2006 | Everett et al. | | |

(Continued)

FOREIGN PATENT DOCUMENTS

| | | |
|---|---|---|
| JP | 2008-528954 A | 7/2008 |
| JP | 2017-522066 A | 8/2017 |

(Continued)

OTHER PUBLICATIONS

European Search Report for EP Patent Application No. 22214175.6, Issued on Jun. 6, 2023, 7 pages.

*Primary Examiner* — Michelle M Iacoletti
*Assistant Examiner* — Alexandria Mendoza
(74) *Attorney, Agent, or Firm* — Faegre Drinker Biddle & Reath LLP

(57) ABSTRACT

A Fourier-domain optical coherence tomography imaging system (10) comprising an Fourier-domain optical coherence tomography scanner (20) arranged to generate complex optical coherence tomography data (25) by performing a scan of an imaging target (30) to acquire samples whose complex values are indicative of an optical property of the imaging target at respective scan locations in the imaging target. The imaging system (10) further comprises a controller (40) arranged to calculate a two-dimensional cross-correlation using phase information of the acquired samples, and control the scanner (20), based on the calculated cross-correlation, to compensate for relative movement between the imaging target (30) and the scanner (20) during the scan.

20 Claims, 17 Drawing Sheets

(51) Int. Cl.

| | |
|---|---|
| ***G01B 9/02055*** | (2022.01) |
| ***G01B 9/02091*** | (2022.01) |
| ***G16H 40/63*** | (2018.01) |

(58) Field of Classification Search

CPC ............ G01B 9/02067; G01B 9/02043; G01B 9/02077; G01B 9/02044; G16H 40/63; G11B 7/0906

See application file for complete search history.

(56) References Cited

U.S. PATENT DOCUMENTS

| | | | | |
|---|---|---|---|---|
| 2006/0187462 | A1 | 8/2006 | Srinivasan et al. | |
| 2013/0010259 | A1 | 1/2013 | Carnevale | |
| 2015/0159992 | A1 | 6/2015 | Buckland et al. | |
| 2016/0040977 | A1* | 2/2016 | An ..................... | G01B 9/02077 356/479 |
| 2016/0338589 | A1* | 11/2016 | Carrasco-Zevallos ....................... | A61B 3/102 |
| 2017/0105618 | A1 | 4/2017 | Schmoll et al. | |
| 2021/0007601 | A1 | 1/2021 | Schmoll et al. | |
| 2022/0142472 | A1 | 5/2022 | Ashok et al. | |
| 2022/0214156 | A1* | 7/2022 | Shibayama .............. | A61B 3/10 |

FOREIGN PATENT DOCUMENTS

| | | | | |
|---|---|---|---|---|
| JP | 2022-077988 | A | 5/2022 | |
| WO | WO-2022106544 | A1 * | 5/2022 | ............. A61B 3/152 |

* cited by examiner

IMAGING TARGET MOVEMENT COMPENSATION IN A FOURIER-DOMAIN OPTICAL COHERENCE TOMOGRAPHY IMAGING SYSTEM

FIELD

Example aspects herein generally relate to the field of Fourier-domain optical coherence tomography (FD-OCT) imaging systems and, in particular, to techniques for compensating for a relative movement between an imaging target and an FD-OCT scanner during a scan of the imaging target by the FD-OCT scanner.

BACKGROUND

Optical coherence tomography (OCT) is an imaging technique based on low-coherence interferometry, which is widely used to acquire high-resolution two- and three-dimensional images of optical scattering media, such as biological tissue.

As is well-known, OCT imaging systems can be classified as being time-domain OCT (TD-OCT) or Fourier-domain OCT (FD-OCT) (also referred to as frequency-domain OCT), depending on how depth ranging is achieved. In TD-OCT, an optical path length of a reference arm of the imaging system's interferometer is varied in time during the acquisition of a reflectivity profile of the scattering medium being imaged by the OCT imaging system (referred to herein as the "imaging target"), the reflectivity profile being commonly referred to as a "depth scan" or "axial scan" ("A-scan"). In FD-OCT, a spectral interferogram resulting from an interference between the reference arm and the sample arm of the interferometer at each A-scan location is Fourier transformed to simultaneously acquire all points along the depth of the A-scan, without requiring any variation in the optical path length of the reference arm. FD-OCT can allow much faster imaging than scanning of the sample arm mirror in the interferometer, as all the back reflections from the sample are measured simultaneously. Two common types of FD-OCT are spectral-domain OCT (SD-OCT) and swept-source OCT (SS-OCT). In SD-OCT, a broadband light source delivers many wavelengths to the imaging target, and all wavelengths are measured simultaneously using a spectrometer as the detector. In SS-OCT (also referred to as time-encoded frequency-domain OCT), the light source is swept through a range of wavelengths, and the temporal output of the detector is converted to spectral interference.

OCT imaging systems can also be classified as being point-scan (also known as "point detection" or "scanning point"), line-scan or full-field, depending on how the imaging system is configured to acquire OCT data laterally. A point-scan OCT imaging system acquires OCT data by scanning a focused sample beam across the surface of the imaging target, typically along a single line (which may be straight, or alternatively curved so as to define a circle or a spiral, for example) or along a set of (usually substantially parallel) lines on the surface of the imaging target, and acquiring an axial depth profile (A-scan) for each of a plurality of points along the line(s), one single point at a time, to build up OCT data comprising a one- or two-dimensional array of A-scans representing a two-dimensional or three-dimensional (volumetric) reflectance profile of the sample.

Despite technological improvements that have allowed OCT imaging systems to acquire sample image data at ever increasing speeds, involuntary eye movements (e.g. micro saccades) during imaging remain a significant cause of artifacts in OCT images, even in ultrahigh-speed systems. Although post-processing algorithms have been developed to remove artefacts of such eye movements, this approach may not adequately deal with large and rapid eye movements, which can lead to gaps in the acquired OCT data that cannot be compensated for in post-processing. More effective approaches to reducing eye motion artifacts employ a second (fast) imaging modality, such as a scanning laser ophthalmoscope (SLO) or a fundus camera, for example, to acquire intensity-based retinal images for monitoring movements of an imaged region of the retina during OCT imaging, and use an eye motion signal acquired therefrom to control the OCT scanning mirror(s) to maintain the OCT scanning grid on target.

SUMMARY

There is provided, in accordance with a first example aspect herein, a Fourier-domain optical coherence tomography (FD-OCT) imaging system comprising: an FD-OCT scanner arranged to generate complex OCT data by performing a scan of an imaging target to acquire samples whose complex values are indicative of an optical property of the imaging target at respective scan locations in the imaging target; and a controller arranged to perform a cross-correlation calculation that uses phase information of the acquired samples, and control the FD-OCT scanner, based on the cross-correlation calculation, to compensate for a relative movement between the imaging target and the FD-OCT scanner during the scan.

In an example embodiment of the FD-OCT imaging system of the first example aspect, the controller may be arranged to perform the cross-correlation calculation by: acquiring a first set of the samples, the samples of the first set comprising samples that have been acquired by the FD-OCT scanner scanning the imaging target along a first scan line on the imaging target; acquiring a second set of the samples, the samples of the second set comprising samples that have been acquired by the FD-OCT scanner scanning the imaging target along a second scan line on the imaging target, wherein the second scan line at least partially overlaps the first scan line; and performing the cross-correlation calculation to calculate a cross-correlation between a third set of samples comprising at least some samples of the first set of samples, and a fourth set of samples comprising at least some samples of the second set of samples, at least some samples of the third set of samples and at least some samples of the fourth set of samples having been acquired from a common region of the imaging target at which the first scan line and the second scan line overlap, the cross-correlation calculation being based on phase information in the third set of samples and phase information in the fourth set of samples. In the example embodiment, the controller may further be arranged to control the FD-OCT scanner to compensate for the relative movement between the imaging target and the FD-OCT scanner during the scan by: registering the first set of samples and the second set of samples with respect to each other using the calculated cross-correlation to determine a value of an offset indicator that is indicative of an offset between scan locations of the first set of samples and scan locations of the second set of samples; and using the determined value of the offset indicator to control the FD-OCT scanner, during the scan, to compensate for a relative movement between the imaging target and the FD-OCT scanner that occurred between the acquisition of the first set of samples and the acquisition of the second set of samples by the FD-OCT scanner.

In a first variant of the example embodiment set out above, the FD-OCT scanner may be arranged to generate the complex OCT data by performing, as the scan, repeat linear scans of the imaging target along overlapping scan lines on the imaging target, such that the acquired samples define repeat B-scans of the imaging target. In the first variant, the controller may be arranged to perform the cross-correlation calculation by: acquiring, as the first set of the samples, a first B-scan of the repeat B-scans; acquiring, as the second set of the samples, a second B-scan of the repeat B-scans; and performing, as the cross-correlation calculation, a cross-correlation calculation to calculate a cross-correlation between one or more A-scans of the first B-scan, and A-scans of the second B-scan, wherein the A-scans of the second B-scan include A-scans that are correspondingly located in the second B-scan to the one or more A-scans in the first B-scan. In the first variant, the controller may further be arranged to control the FD-OCT scanner to compensate for the relative movement between the imaging target and the FD-OCT scanner during the scan by: registering the first B-scan, as the first set of samples, and the second B-scan, as the second set of samples, with respect to each other, by using the calculated cross-correlation to determine, as the value of the offset indicator, an offset value that is indicative of an offset between the first B-scan and the second B-scan; and controlling the FD-OCT scanner to compensate for a relative movement between the imaging target and the FD-OCT scanner that occurred between the acquisition of the first B-scan and the acquisition of the second B-scan by the FD-OCT scanner, by using the determined offset value.

In the first variant set out above, the controller may be arranged to perform, as the cross-correlation calculation, a cross-correlation calculation to calculate a cross-correlation between a predetermined number of A-scans of the first B-scan, and A-scans of the second B-scan, the cross-correlation calculation being based on phase information in the predetermined number of A-scans of the first B-scan and phase information in the A-scans of the second B-scan, wherein the predetermined number is selected such that a variation of the phase information among the predetermined number of A-scans of the first B-scan is less than a predetermined degree of variation. In this case, the controller may further be arranged to control the FD-OCT scanner to compensate for the relative movement between the imaging target and the FD-OCT scanner during the scan by: performing a plurality of the cross-correlation calculations to calculate a respective cross-correlation between each set of a plurality of sets of the predetermined number of A-scans of the first B-scan and respective A-scans of the second B-scan, the respective A-scans of the second B-scan including A-scans that are correspondingly located in the second B-scan to the predetermined number of A-scans in the set; combining the calculated cross-correlations to determine, as the offset value, a value that is indicative of an offset between the first B-scan and the second B-scan; and controlling the FD-OCT scanner to compensate for the relative movement between the imaging target and the FD-OCT scanner by using the determined offset value that is indicative of the offset between the first B-scan and the second B-scan.

In a second variant of the FD-OCT imaging system of the above example embodiment, the FD-OCT scanner may be arranged to generate the complex OCT data by performing, as the scan, an area OCT scan of the imaging target comprising samples having complex values that are indicative of the optical property of the imaging target at respective scan locations that are distributed three-dimensionally in the imaging target, and the controller may be arranged to perform the cross-correlation calculation by acquiring, as the first set of samples, a set of samples comprising samples which have been acquired by the FD-OCT scanner scanning the imaging target along the first scan line as at least a part of the area OCT scan, wherein the second scan line crosses the first scan line obliquely.

In the second variant, the first scan line may be one of a plurality of parallel scan lines on the imaging target, the FD-OCT scanner being arranged to perform the area OCT scan by scanning the imaging target along the plurality of parallel scan lines, and to generate an OCT C-scan as the complex OCT data, based on the area OCT scan. The controller may be arranged to perform the cross-correlation calculation by acquiring, as the first set of samples, the complex OCT data of the C-scan.

Alternatively, in the second variant, the first scan line may extend along two dimensions on a surface of the imaging target, and may define, for example, a square, a triangle, a diamond, a circle, an ellipse, a spiral, a square spiral, a Lissajous figure, an epitrochoid, or a hypotrochoid on the surface of the imaging target.

As a further alterative, in the second variant, the first scan line and the second scan line may be different respective parts of a single scan line, which extends along two dimensions on a surface of the imaging target and crosses (intersects) itself. The single scan line may define a Lissajous figure, an epitrochoid, or a hypotrochoid on the surface of the imaging target, for example.

There is provided, in accordance with a second example aspect herein, a computer-implemented method of controlling a FD-OCT scanner, which is generating complex OCT data by performing a scan of an imaging target to acquire samples whose complex values are indicative of an optical property of the imaging target at respective scan locations in the imaging target, to compensate for a relative movement between the imaging target and the FD-OCT scanner during the scan. The method comprises performing a cross-correlation calculation that uses phase information of the acquired samples, and controlling the FD-OCT scanner, based on the cross-correlation calculation, to compensate for the relative movement between the imaging target and the FD-OCT scanner during the scan.

In an example embodiment of the computer-implemented method of the second example aspect, the cross-correlation calculation may be performed by: acquiring a first set of the samples, the samples of the first set comprising samples that have been acquired by the FD-OCT scanner scanning the imaging target along a first scan line on the imaging target; acquiring a second set of the samples, the samples of the second set comprising samples that have been acquired by the FD-OCT scanner scanning the imaging target along a second scan line on the imaging target, wherein the second scan line at least partially overlaps the first scan line; and performing the cross-correlation calculation to calculate a cross-correlation between a third set of samples comprising at least some samples of the first set of samples, and a fourth set of samples comprising at least some samples of the second set of samples, at least some samples of the third set of samples and at least some samples of the fourth set of samples having been acquired from a common region of the imaging target at which the first scan line and the second scan line overlap, the cross-correlation calculation being based on phase information in the third set of samples and phase information in the fourth set of samples. Furthermore, in the example embodiment of the computer-implemented method of the second example aspect, the FD-OCT scanner may be controlled to compensate for the relative movement between the imaging target and the FD-OCT scanner during the scan by: registering the first set of samples and the second set of samples with respect to each other using the calculated cross-correlation to determine a value of an offset indicator that is indicative of an offset between scan locations of the first set of samples and scan locations of the second set of samples; and using the determined value of the offset indicator to control the FD-OCT scanner, during the scan, to compensate for a relative movement between the imaging target and the FD-OCT scanner that occurred between the acquisition of the first set of samples and the acquisition of the second set of samples by the FD-OCT scanner.

In a first variant of the example embodiment of the computer-implemented method set out above, the FD-OCT scanner may generate the complex OCT data by performing, as the scan, repeat linear scans of the imaging target along overlapping scan lines on the imaging target, such that the acquired samples define repeat B-scans of the imaging target, and the method may comprise performing the cross-correlation calculation by: acquiring, as the first set of the samples, a first B-scan of the repeat B-scans; acquiring, as the second set of the samples, a second B-scan of the repeat B-scans; and performing, as the cross-correlation calculation, a cross-correlation calculation to calculate a cross-correlation between one or more A-scans of the first B-scan, and A-scans of the second B-scan, wherein the A-scans of the second B-scan include A-scans that are correspondingly located in the second B-scan to the one or more A-scans in the first B-scan. The method may comprise controlling the FD-OCT scanner to compensate for the relative movement between the imaging target and the FD-OCT scanner during the scan by: registering the first B-scan, as the first set of samples, and the second B-scan, as the second set of samples, with respect to each other, by using the calculated cross-correlation to determine, as the value of the offset indicator, an offset value that is indicative of an offset between the first B-scan and the second B-scan; and controlling the FD-OCT scanner to compensate for a relative movement between the imaging target and the FD-OCT scanner that occurred between the acquisition of the first B-scan and the acquisition of the second B-scan by the FD-OCT scanner, by using the determined offset value.

The method of the first variant as set out above may comprise performing, as the cross-correlation calculation, a cross-correlation calculation to calculate a cross-correlation between a predetermined number of A-scans of the first B-scan, and A-scans of the second B-scan, the cross-correlation calculation being based on phase information in the predetermined number of A-scans of the first B-scan and phase information in the A-scans of the second B-scan, wherein the predetermined number is selected such that a variation of the phase information among the predetermined number of A-scans of the first B-scan is less than a predetermined degree of variation. The FD-OCT scanner may be controlled to compensate for the relative movement between the imaging target and the FD-OCT scanner during the scan by: performing a plurality of the cross-correlation calculations to calculate a respective cross-correlation between each set of a plurality of sets of the predetermined number of A-scans of the first B-scan and respective A-scans of the second B-scan, the respective A-scans of the second B-scan including A-scans that are correspondingly located in the second B-scan to the predetermined number of A-scans in the set; combining the calculated cross-correlations to determine, as the offset value, a value that is indicative of an offset between the first B-scan and the second B-scan; and controlling the FD-OCT scanner to compensate for the relative movement between the imaging target and the FD-OCT scanner by using the determined offset value that is indicative of the offset between the first B-scan and the second B-scan.

Alternatively, in a computer-implemented method of a second variant of the example embodiment set out above, the FD-OCT scanner may generate the complex OCT data by performing, as the scan, an area OCT scan of the imaging target to acquire samples having complex values that are indicative of the optical property of the imaging target at respective scan locations that are distributed three-dimensionally in the imaging target, and the method may comprise performing the cross-correlation calculation by acquiring, as the first set of samples, a set of samples comprising samples which have been acquired by the FD-OCT scanner scanning the imaging target along the first scan line as at least a part of the area OCT scan, wherein the second scan line crosses the first scan line obliquely. The first scan line may be one of a plurality of parallel scan lines on the imaging target, wherein the FD-OCT scanner performs the area OCT scan by scanning the imaging target along the plurality of parallel scan lines, and generates an OCT C-scan as the complex OCT data, based on the area OCT scan. In this case, the cross-correlation calculation may comprise acquiring, as the first set of samples, the complex OCT data of the C-scan.

Alternatively, in the computer-implemented method of the second variant, the first scan line may extend along two dimensions on a surface of the imaging target, and may define, for example, a square, a triangle, a diamond, a circle, an ellipse, a spiral, a square spiral, a Lissajous figure, an epitrochoid, or a hypotrochoid on the surface of the imaging target.

As a further alterative, in the computer-implemented method of the second variant, the first scan line and the second scan line may be different respective parts of a single scan line, which extends along two dimensions on a surface of the imaging target and crosses (intersects) itself. The single scan line may define a Lissajous figure, an epitrochoid, or a hypotrochoid on the surface of the imaging target, for example.

There is also provided, in accordance with a third example aspect herein, a computer program comprising computer-readable instructions which, when executed by a processor, which is controlling a FD-OCT scanner to generate complex OCT data by performing a scan of an imaging target to acquire samples whose complex values are indicative of an optical property of the imaging target at respective scan locations in the imaging target, cause the processor to control the FD-OCT scanner to compensate for a relative movement between the imaging target and the FD-OCT scanner during the scan, by performing the method according to the second example aspect, its example embodiment or any of the variants thereof set out above. The computer program may be stored on a non-transitory computer-readable storage medium (such as a computer hard disk or a CD, for example) or carried by a computer-readable signal.

BRIEF DESCRIPTION OF THE DRAWINGS

Example embodiments will now be explained in detail, by way of non-limiting example only, with reference to the accompanying figures described below. Like reference numerals appearing in different ones of the figures can denote identical or functionally similar elements, unless indicated otherwise.

DETAILED DESCRIPTION OF EXAMPLE EMBODIMENTS

Figure 1:
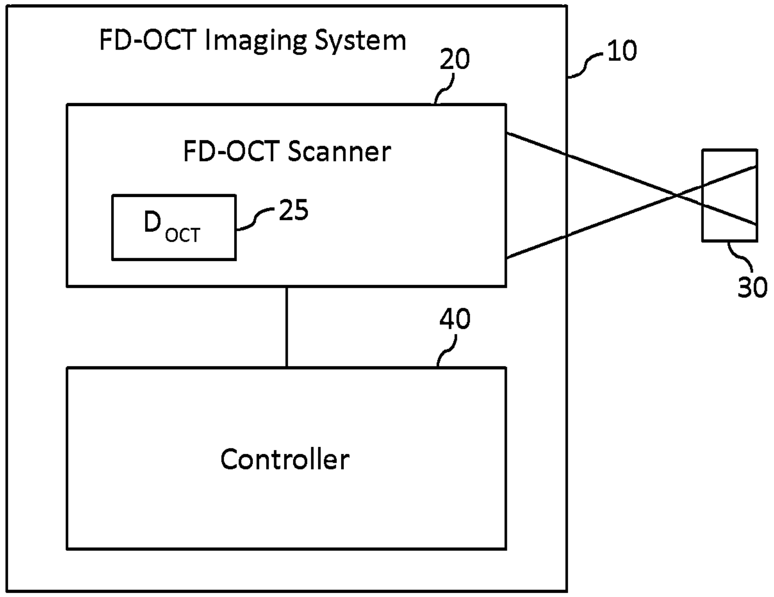
FIG. 1 is a schematic illustration of a Fourier-domain OCT imaging system according to an example embodiment herein.

In view of the background discussed above, the inventors have devised a scheme for at least partially avoiding motion artifacts in OCT data acquired during a FD-OCT scan, without requiring post-processing algorithms of the kind described above for artefact removal that have the noted shortcomings, or a second imaging modality to provide tracking of the imaging target for motion compensation. More particularly, the inventors have recognised that the phase information in complex OCT data acquired by a FD-OCT imaging system can provide a detailed and reproducible 'fingerprint' of the imaged structure, which can be acquired and used quickly enough to enable motion tracking and real-time control of the OCT data acquisition process to compensate for a relative movement between the FD-OCT imaging system and the imaging target. The inventors have accordingly devised a Fourier-domain OCT imaging system comprising: an FD-OCT scanner arranged to generate complex OCT data by performing a scan of an imaging target to acquire samples whose complex values are indicative of an optical property of the imaging target at respective scan locations in the imaging target; and a controller arranged to perform a cross-correlation calculation that uses phase information of the acquired samples, and control the FD-OCT scanner, based on the cross-correlation calculation, to compensate for a relative movement between the imaging target and the FD-OCT scanner during the scan.

The controller may perform the cross-correlation calculation using a first set of samples and a second set of samples which may, for example, have been acquired by the FD-OCT scanner scanning a sample light beam along a first scan line on the imaging target and along a second, partially overlapping scan line on the imaging target, respectively. The scan lines are virtual lines (which may be curved or straight) representing a path on a surface of the imaging target which is followed by the light beam during the scan. The first set of samples and the second set of samples may be acquired from one or more scans taken along a first scan line and a second scan line that may be provided in one of a number of different forms, as described in the example embodiments below. For example, the first and second scan lines may fully overlap and be followed by the light beam in different respective scans that are performed by the FD-OCT scanner, for example in the case of the FD-OCT scanner acquiring repeat B-scans of an imaged section of the imaging target, as in the first example embodiment below. The first and second scan lines may alternatively cross each other at one or more discrete points on the imaging target and be followed by the light beam in separate scans (for example, in a preliminary "reference" scan, and a subsequent "measurement" scan) that are performed by the FD-OCT scanner. As a further alternative, the first and second scan lines may cross each other at one or more points on the surface of the imaging target, and form parts of a single, continuous ("self-referencing") scan being performed by the FD-OCT scanner. These alternatives are described in more detail below, in relation to the second example embodiment.

Example embodiments of the FD-OCT imaging system will now be described in detail, with reference to accompanying drawings.

First Example Embodiment

FIG. 1 is a schematic illustration of a FD-OCT imaging system 10 according to a first example embodiment. The FD-OCT imaging system 10 comprises a FD-OCT scanner (OCT scanning and data acquisition system) 20, which is arranged to generate complex OCT data 25 by performing a scan of an imaging target 30 to acquire samples whose complex values are indicative of an optical property (e.g. reflectivity or reflectance) of the imaging target 30 at respective scan locations in the imaging target 30.

The FD-OCT scanner 20 may, as in the present example embodiment, be a swept-source OCT (SS-OCT) system. However, the FD-OCT scanner 20 need not be provided in this form and may, for example, take the alternative form of a spectral-domain OCT (SD-OCT). More generally, an example embodiment may be provided as any form of FD-OCT imaging system that is capable of generating complex OCT data 25, i.e. Fourier transforms of respective spectral interferograms (interference spectra) representing complex A-scan information obtained for each scan location at which an OCT measurement is made during the scan. Such complex OCT data 25 encodes phase information from acquired OCT measurements that can be used by the controller 40 as described herein to compensate for relative movements between the FD-OCT scanner 20 and the imaging target 30 whilst a scan of the imaging target 30 is being performed by the FD-OCT scanner 20.

Figure 2:
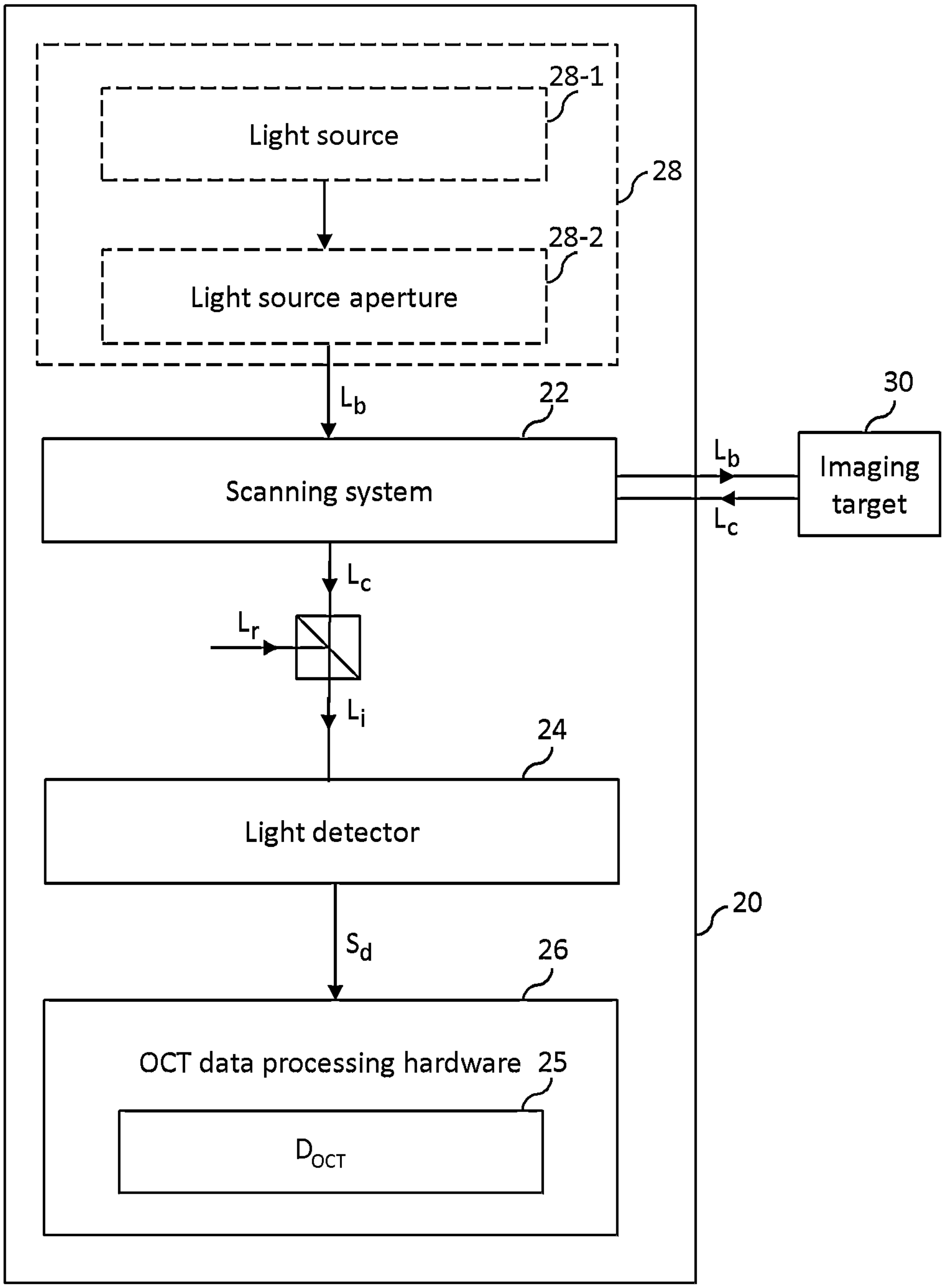
FIG. 2 is a schematic illustration of components of the FD-OCT scanner employed in the example embodiment.

The FD-OCT scanner 20 may include well-known components, including a scanning system 22, a light detector 24, OCT data processing hardware 26, and a light beam generator 28, as illustrated in FIG. 2.

The scanning system 22 may be arranged to perform a one- and/or two-dimensional point-scan of a light beam $L_b$ across an imaging target 30, and collect light $L_c$ which has been scattered by the imaging target 30 during the point scan. The scanning system 22 is therefore arranged to acquire A-scans at respective scan locations that are distributed across a surface of the imaging target 30, by sequentially illuminating the scan locations with the light beam $L_b$, one scan location at a time, and collecting at least some of the light $L_c$ scattered by the imaging target 30 at each scan location. The scanning system 22 may perform the point-scan using any suitable scan pattern known to those versed in the art, for example a unidirectional scan (wherein a set of (e.g. parallel or overlapping) scan lines are followed in a common direction, along which they extend), a serpentine scan or spiral scan. Although the scanning system 22 is arranged to perform point-scans in the present example embodiment, the scanning system 22 may alternatively be arranged to perform line-scans in other example embodiments, using hardware well-known to those versed in the art.

In the present example embodiment, the FD-OCT imaging system 10 is an ophthalmic FD-OCT imaging system, which is arranged to acquire OCT data from an imaging target 30 in the form of a region of a retina of an eye, although any other part of the eye that can be imaged by OCT, such as a portion of the anterior segment of the eye, may alternatively or additionally form the imaging target 30. The imaging target 30 is not, however, limited to a portion of an eye and may alternatively be any tissue (e.g. skin), biological sample or, more generally, any scattering medium whose sub-subsurface structure is to be imaged by OCT.

The light beam generator 28 may include a light source 28-1 and a light source aperture 28-2. In this case, the light source 28-1 is arranged to emit light through the light source aperture 28-1 to generate the light beam $L_b$, such that the shape and size (e.g. diameter, in case of the light source aperture 28-2 being circular) of the light source aperture 28-2 defines the cross-sectional shape and size (e.g. diameter) of the light beam $L_b$ (i.e. so that these sizes and shapes are the same). In some example embodiments, the light beam generator 28 may comprise further components (not shown in FIG. 2), such as one or more collimating lenses for collimating light from the light source 28-1, for example.

The light detector 24 is arranged to generate a detection signal $S_d$ based on an interference light $L_i$ resulting from an interference between a reference light $L_r$ and the light $L_c$ collected by the scanning system 22 during the scan. In other words, the reference light and the light collected by the scanning system during the point scan are guided to coincide and interfere with one another, and the resulting interference light $L_i$ is directed to and received by light detecting components (not shown) of the light detector 24. The light detector 24 generates the detection signal $S_d$ by performing photoelectric conversion of the received interference light $L_i$. The specific form which the light detector 24 may take will depend on the form in which the FD-OCT scanner 20 is implemented. For example, where the FD-OCT scanner 20 is implemented as an SD-OCT scanner, the light detector 24 comprises a spectrometer, which may have a diffraction grating, Fourier transform lend, and a detector array (or a line scan camera). Where the FD-OCT scanner 20 is implemented as a SS-OCT scanner, as in the present example embodiment, the light detector 24 may comprise a balanced photodetector set-up comprising two photodetectors (e.g. reverse-biased photodiodes), whose output photocurrents are subtracted from one another, with the subtracted current signal being converted into a voltage detection signal by a transimpedance amplifier.

The detection signal $S_d$ is then processed by the OCT data processing hardware 26. The OCT data processing hardware 26 is arranged to generate complex OCT data of the imaging target 30, based on the detection signal $S_d$, using well-known data processing techniques.

Referring again to FIG. 1, the FD-OCT imaging system 10 further comprises a controller 40, which is arranged to perform a complex cross-correlation calculation to calculate a complex cross-correlation between acquired samples, using phase information of the acquired samples. The controller 40 is further arranged to control the FD-OCT scanner 20, based on the result of the cross-correlation calculation, to compensate for a relative movement between the imaging target 30 and the FD-OCT scanner 20 during the scan.

The FD-OCT scanner 20 may, as in the present example embodiment, be arranged to acquire samples of the complex OCT data 25 by scanning the imaging target 30 along one or more scan lines on a surface of the imaging target 30, and the controller 40 may be arranged to perform the cross-correlation calculation firstly by acquiring sets of samples of the complex OCT data 25. More particularly, the controller 40 may acquire a first set of the samples, wherein the samples of the first set comprise samples that have been acquired by the FD-OCT scanner 20 scanning the imaging target 30 along a first scan line on the surface of the imaging target 30, and acquire a second set of the samples, wherein the samples of the second set comprise samples that have been acquired by the FD-OCT scanner 20 scanning the imaging target 30 along a second scan line on the imaging target 30, where the second scan line at least partially overlaps the first scan line. The samples of the first set of samples may, as in the present example embodiment, comprise first A-scans and a respective indication of a scan location on the imaging target 30 at which each A-scan of the first A-scans was acquired. Likewise, the samples of the second set of samples may, as in the present example embodiment, comprise second A-scans and a respective indication of a scan location on the imaging target 30 at which each A-scan of the second A-scans was acquired.

The FD-OCT scanner 20 may acquire such first and second sets of samples by scanning the imaging target 30 in one of several different ways, for example by being pre-configured to perform a particular type of scan by which the first and second sets of samples can be acquired, or by being operable in several different operational modes, wherein at least some of those modes allow the FD-OCT scanner 20 to acquire the first and second sets of samples. The first and second scan lines on the surface of the imaging target may, for example, fully overlap and be followed by the light beam $L_b$ in separate scans that are performed by the FD-OCT scanner 20 (e.g. in the case of the FD-OCT scanner 20 acquiring repeat B-scans of an imaged section of the imaging target 30). The first and second scan lines may alternatively cross each other at one or more points on the surface of the imaging target 30, and be followed by the light beam $L_b$ in separate scans (for example, in a preliminary "reference" scan, and a subsequent "measurement" scan) that are performed by the FD-OCT scanner 20. As a further alternative, the first and second scan lines may cross each other at one or more points on the surface of the imaging target 30, and form parts of a single, continuous ("self-referencing") scan being performed by the FD-OCT scanner 20. These alternative scanning schemes are described in more detail below.

Once these sets of samples have been acquired, the controller 40 performs the cross-correlation calculation to calculate a (at least two-dimensional) cross-correlation between a third set of samples, comprising at least some samples of the first set of samples, and a fourth set of samples, comprising at least some samples of the second set of samples, wherein at least some samples of the third set of samples and at least some samples of the fourth set of samples were acquired from a common region of the imaging target 30, at which the first scan line and the second scan line overlap. The cross-correlation calculation is based on phase information in the third set of samples and phase information in the fourth set of samples and may, more specifically, be a cross-correlation between phase information in the third set of samples and phase information in the fourth set of samples.

The controller 40 is arranged to control the FD-OCT scanner 20 to compensate for the relative movement between the imaging target 30 and the FD-OCT scanner 20 during the scan firstly by registering the first set of samples and the second set of samples with respect to each other using the calculated cross-correlation. The controller 40 uses this process to determine a value of an offset indicator that is indicative of an offset (i.e. displacement or translation) between scan locations of the first set of samples and scan locations of the second set of samples, which has been caused by a relative movement between the FD-OCT scanner 20 and the imaging target 30 during the scan, between the acquisition of the first set of samples and the acquisition of the second set of samples by the FD-OCT scanner 20. The controller 40 is further arranged to use the determined value of the offset indicator to control the FD-OCT scanner 20, during the scan, to compensate for the relative movement. The controller 40 may achieve this by causing the scanning system 22 of the FD-OCT scanner 20 to adjust one or more scan parameters that determine the movement of one or more scanning elements that scan the light beam $L_b$ across an imaging target 30 so as to at least partly counter the offset indicated by the offset indicator, such that a subsequent repeat scan defined by the scan parameters used in the previous scan along the second scan line, as adjusted on the basis of the offset indicator, would yield a smaller offset between scan locations of the first set of samples and scan locations of the subsequently acquired set of samples than the offset between scan locations of the first set of samples and scan locations of the second set of samples.

Figure 3:
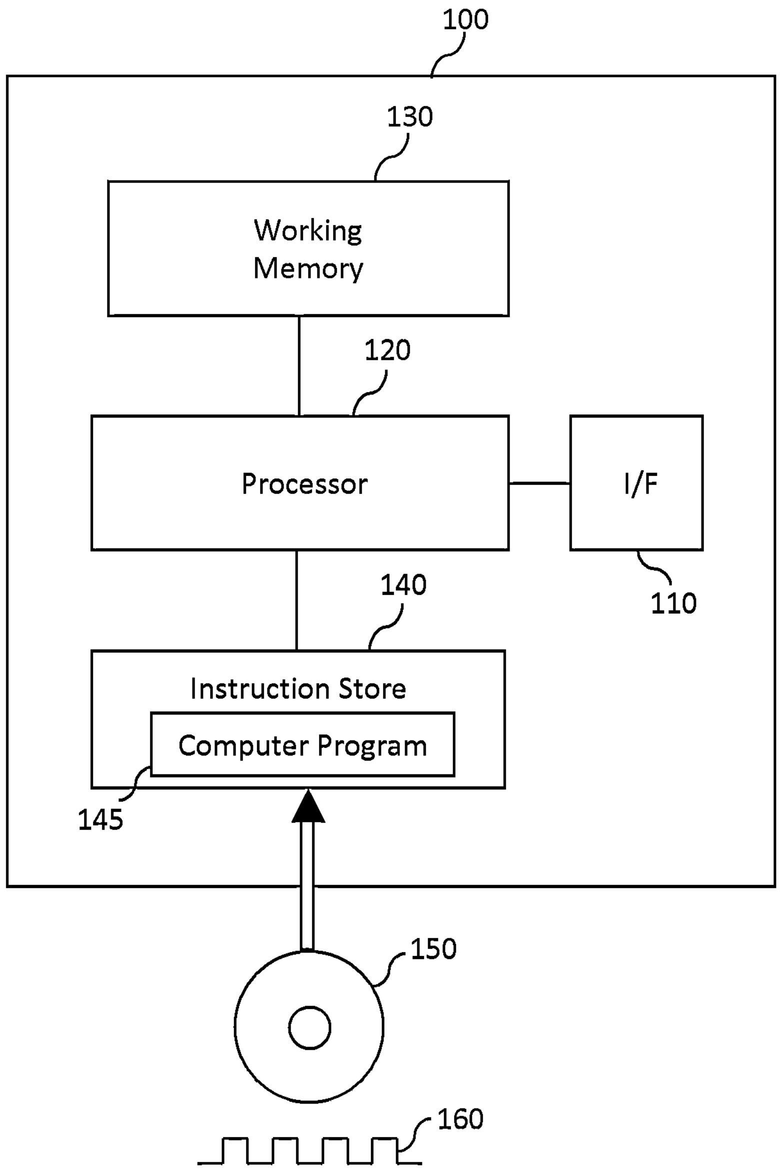
FIG. 3 is a schematic illustration of a programmable signal processing hardware, which may be configured to perform the functions of the controller described herein.

The OCT data processing hardware 26 and the controller 40 may be provided in any suitable form. By way of an example, both these components are implemented in the form of a (single) programmable signal processing hardware 100 of the kind illustrated schematically in FIG. 3. It should be noted, however, that the OCT data processing hardware 26 and the controller 40 may alternatively each be implemented in respective (separate) programmable signal processing hardware 100 of the kind illustrated in FIG. 3. Furthermore, one or both these components may alternatively be implemented in non-programmable hardware, such as an ASIC, an FPGA or other integrated circuit dedicated to performing the functions of the OCT data processing hardware 26 and/or the controller 40 (as the case may be), or a combination of such non-programmable hardware and programmable hardware as described above with reference to FIG. 3.

The programmable signal processing apparatus 100 comprises a communication interface (I/F) 110, for receiving the detection signal $S_d$ from the light detector 24, and outputting control signals for controlling the FD-OCT scanner 20 (specifically, the scanning system 22 thereof) to compensate for a relative movement between the imaging target 30 and the FD-OCT scanner 20 during the scan. The signal processing hardware 100 further comprises a processor (e.g. a Central Processing Unit, CPU, and/or a Graphics Processing Unit, GPU) 120, a working memory 130 (e.g. a random-access memory) and an instruction store 140 storing a computer program 145 comprising the computer-readable instructions which, when executed by the processor 120, cause the processor 120 to perform various functions including those of the OCT data processing hardware 26 and the controller 40 described herein. The working memory 130 stores information used by the processor 120 during execution of the computer program 145. The instruction store 140 may comprise a ROM (e.g. in the form of an electrically erasable programmable read-only memory (EEPROM) or flash memory) which is pre-loaded with the computer-readable instructions. Alternatively, the instruction store 140 may comprise a RAM or similar type of memory, and the computer-readable instructions of the computer program 145 can be input thereto from a computer program product, such as a non-transitory, computer-readable storage medium 150 in the form of a CD-ROM, DVDROM, etc. or a computer-readable signal 160 carrying the computer-readable instructions. In any case, the computer program 145, when executed by the processor 120, causes the processor 120 to perform the functions of the controller 40 as described herein. In other words, the controller 40 of the example embodiment may comprise a computer processor 120 and a memory 140 storing computer-readable instructions which, when executed by the computer processor 120, cause the computer processor 120 to control the FD-OCT scanner 20, which is generating complex OCT data 25 by performing a scan of the imaging target 30 to acquire samples whose complex values are indicative of an optical property of the imaging target 30 at respective scan locations in the imaging target 30, to compensate for a relative movement between the imaging target 30 and the FD-OCT scanner 20 during the scan.

Figure 4:
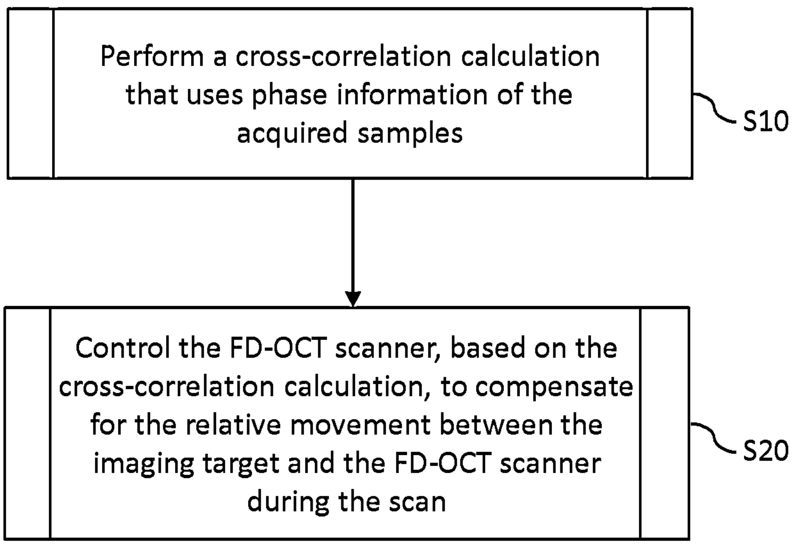
FIG. 4 is a flow diagram illustrating a method of controlling a FD-OCT scanner to compensate for a relative movement between an imaging target and the FD-OCT scanner during a scan, in accordance with an example embodiment.

FIG. 4 is a flow diagram illustrating a process by which the controller 40 of the example embodiment controls the FD-OCT scanner 20, which is generating complex OCT data 25 by performing a scan of an imaging target 30 to acquire samples whose complex values are indicative of an optical property of the imaging target 30 at respective scan locations in the imaging target 30, to compensate for a relative movement between the imaging target 30 and the FD-OCT scanner 20 during the scan.

In process S10 of FIG. 4, the controller 40 performs a cross-correlation calculation that uses phase information of the acquired samples. More specifically, in process S10, the controller 40 calculates a cross-correlation between the phase information in a first set of the samples and a second set of the samples.

In process S20 of FIG. 4, the controller controls the FD-OCT scanner 20, based on the cross-correlation calculation, to compensate for the relative movement between the imaging target 30 and the FD-OCT scanner 20 during the scan. More specifically, in process S20, the controller 40 uses the result of the cross-correlation calculation to modify the scan being performed by the FD-OCT scanner 20 so that, after the modification of the scan, the remainder of the scan is performed with there being no effect, or a reduced effect, of the prior relative movement on samples acquired by the FD-OCT scanner 20 on the remainder of the scan (as compared to the case where the modification of the scan is not performed).

Figure 5:
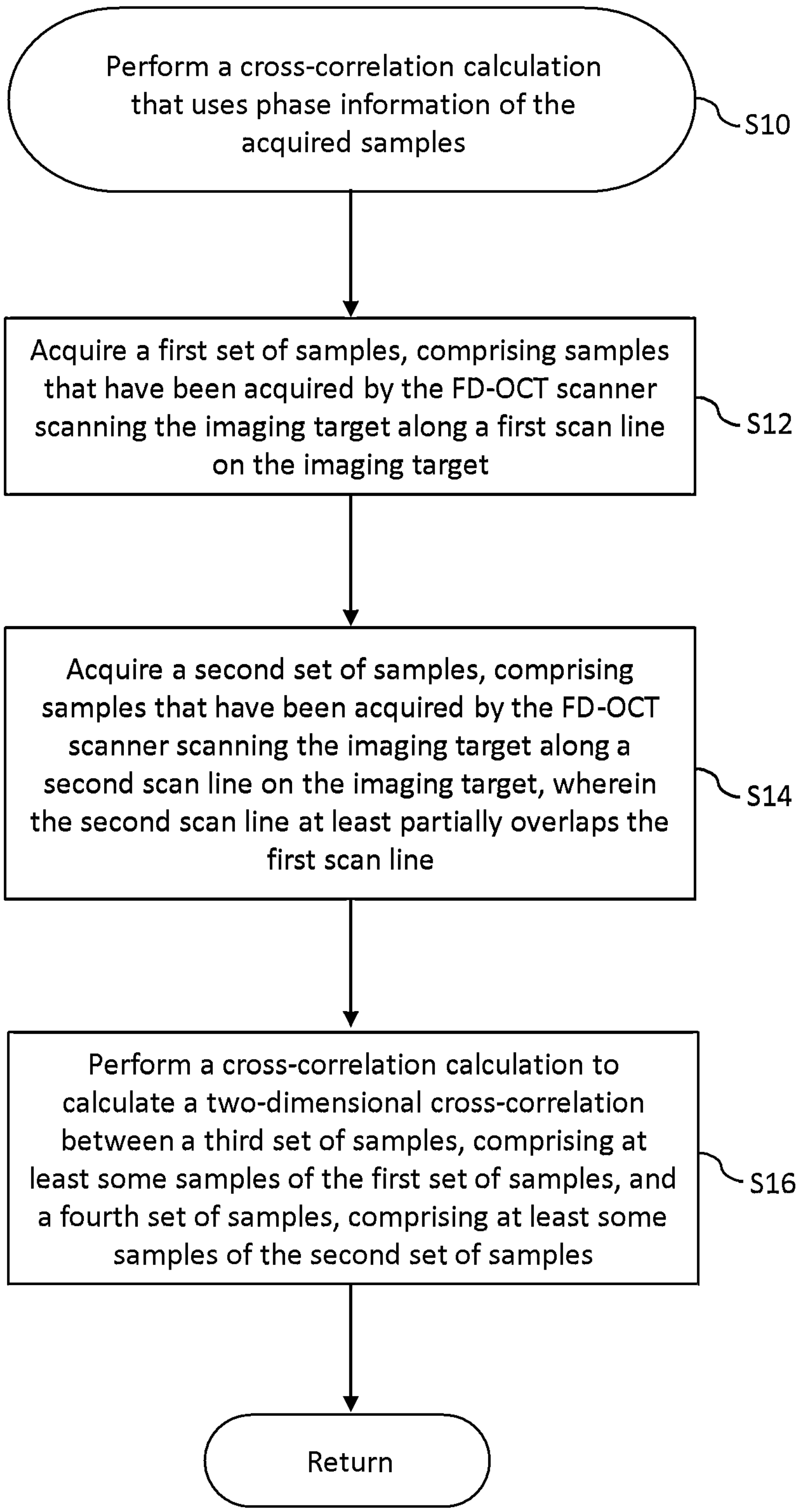
FIG. 5 is a flow diagram illustrating a method by which the cross-correlation calculation of process S10 in FIG. 4 may be performed.

FIG. 5 is a flow diagram illustrating a process by which the controller 40 may perform the cross-correlation calculation in process S10 of FIG. 4.

In process S12 of FIG. 5, the controller 40 acquires a first set of the samples that have been acquired by the FD-OCT scanner 20. The samples of the first set comprises samples that have been acquired by the FD-OCT scanner 20 scanning the imaging target 30 along a first scan line on the imaging target 30. The samples of the first set of samples may, as in the present example embodiment, comprise first A-scans and a respective indication of a scan location on the imaging target 30 at which each A-scan of the first A-scans was acquired.

In process S14 of FIG. 5, the controller 40 acquires a second set of the samples, the samples of the second set comprising samples that have been acquired by the FD-OCT scanner 20 scanning the imaging target 30 along a second scan line on the imaging target 30, wherein the second scan line at least partially overlaps the first scan line. The samples of the second set of samples may, as in the present example embodiment, comprise second A-scans and a respective indication of a scan location on the imaging target 30 at which each A-scan of the second A-scans was acquired.

As noted above, the FD-OCT scanner 20 may acquire such first and second sets of samples by scanning the imaging target 30 in one of several different ways. The FD-OCT scanner 20 may, as in the present example embodiment, generate the complex OCT data 25 by performing, as the scan, repeat linear scans of the light beam $L_b$ over the imaging target 30 along overlapping scan lines on the imaging target 30, such that the acquired samples define repeat B-scans representing respective images of a common cross-section of the imaging target 30. The FD-OCT scanner 40 may thus acquire a first B-scan of the repeat B-scans as the first set of samples, and acquire a second B-scan of the repeat B-scans as the second set of samples.

Figure 6:
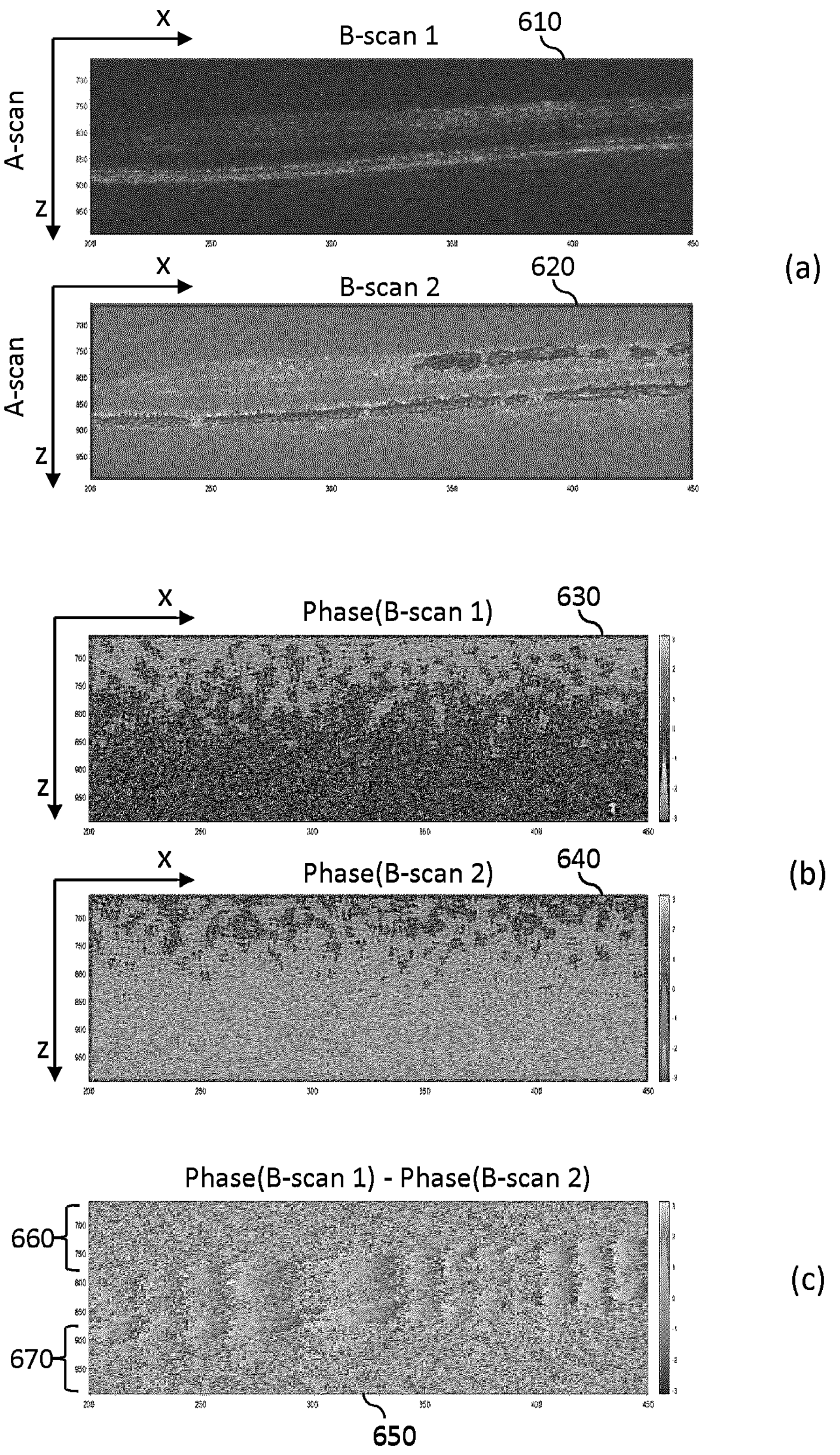
FIG. 6 shows; (a) an example of B-scans processed by the controller of the FD-OCT imaging system of the example embodiment; (b) plots of how the magnitudes of the respective phase component of the B-scans shown in FIG. 6(*a*) vary along x-axis and z-axis directions; and (c) a phase component difference plot obtained by subtracting the phase component values of the B-scan 620 from the phase component values of B-scan 610 of FIG. 6(*a*).

FIG. 6(*a*) shows an example of the first B-scan (B-scan 1) 610 and an example of the second B-scan (B-scan 2) 620, which is the next B-scan in the sequence of repeat B-scans of an imaged section of the retina of an eye (as the imaging target 30) acquired by the FD-OCT scanner 20, after the first B-scan 610. The second B-scan 620 was acquired 0.02 s after the first B-scan 610, although the interval between the B-scans is not so limited. Each of the first B-scan 610 and the second B-scan 620 comprises 200 A-scans arrayed along an x-axis direction, with the data elements in each A-scan being arrayed along a z-axis direction, as illustrated in FIG. 6(*a*). The bands extending across each of the first B-scan 610 and second B-scan 620 in FIG. 6(*a*) correspond to retinal layers of relatively high reflectivity. Such retinal layers may include the external limiting membrane, ellipsoid zone (IS/OS junction), interdigitation zone and the retinal pigment epithelium, for example.

FIG. 6(*b*) shows plots of how the magnitudes of the phase component 630 of the first B-scan 610, and of the phase component 640 in the second B-scan 620, vary along the x-axis and z-axis directions. The phase components 630 and 640 appear to be randomly distributed along the x-axis and z-axis directions, with no pattern being apparent in FIG. 6(*b*).

However, when the phase component values of the second B-scan 620 are subtracted from the phase component values of the first B-scan 610, the resulting phase component difference plot 650 shown in FIG. 6C reveals that the phase information in the two B-scans is strongly correlated, with vertical bands of largely constant difference values being evident in the plot 650 of FIG. 6C. The fluctuations along the z-axis direction are due to relative motion between the imaging target 30 and the FD-OCT scanner 20 during the acquisition of the B-scans. The absence of the bands in the upper region 660 of the plot 650, and in the lower region 670 of the plot 650, arises from the lack of retinal structure (and consequent low signal levels) in the corresponding regions of the first B-scan 610 and the second B-scan 620.

The inventors have recognised that the strong correlation between the phase information in the repeat B-scans 610 and 620 can be used to reliably register the B-scans in a fast and computationally efficient manner. This, in turn, can allow offsets (along the x-axis and/or z-axis directions), which are caused by movements of the imaging target 30 and the FD-OCT scanner 20 relative to each other, to be compensated for in real time, thus allowing effective motion compensation to be provided during a scan performed by the FD-OCT scanner 20, without the need to employ a second imaging modality, such as a scanning laser ophthalmoscope (SLO) or a fundus camera, for this purpose. By the techniques described herein, OCT volumes may be accurately registered at the point spread function width level.

Referring again to FIG. 5, in process S16, the controller 40 performs a complex cross-correlation calculation to calculate a two-dimensional cross-correlation between a third set of samples, which comprises at least some samples of the first B-scan 610 (which B-scan constitutes the aforementioned first set of samples in the present example embodiment), and a fourth set of samples, which comprises at least some samples of the second B-scan 620 (which B-scan constitutes the aforementioned second set of samples in the present example embodiment).

More specifically, the controller 40 may, as in the present example embodiment, calculate a two-dimensional cross-correlation between a predetermined number N of A-scans of the first B-scan 610 (as the third set of samples), and set of A-scans (as the fourth set of samples) of the second B-scan 620, wherein the set of A-scans of the second B-scan 620 include A-scans that are correspondingly located in the second B-scan 620 to the one or more A-scans in the first B-scan 610, and N is an integer greater than or equal to one. The cross-correlation calculation is based on phase information in the third set of samples and phase information in the fourth set of samples. At least some samples of the third set of samples and at least some samples of the fourth set of samples have been acquired from a common region of the imaging target 30, at which the first scan line and the second scan line overlap.

For a third set of samples (here denoted by f), and a fourth set of samples (here denoted by g), the complex cross-correlation between f and g may be expressed as follows: ifftn(fftn(g)*conj(fftn(f))), where "fftn" denotes the fast Fourier transform (FFT), "ifftn" denotes the inverse FFT, and "conj( )" denotes the conjugate.

The complex cross-correlation can be used to identify phase patterns and perform registration due to highly correlated phases when sets of complex OCT data are registered.

Figure 7:
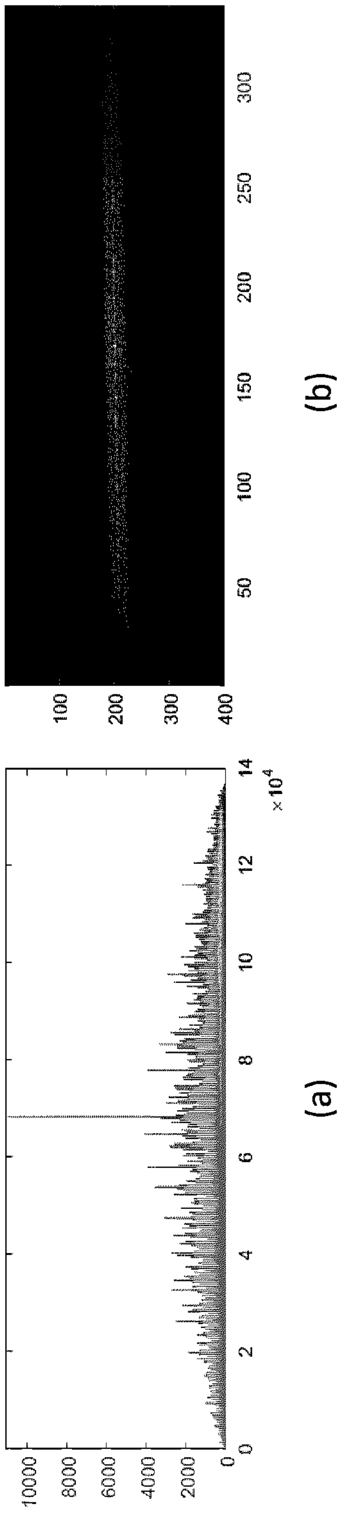
FIG. 7 shows: (a) a cross-correlation graph based on a complex cross-correlation between the complex OCT data of the entire B-scan 610 and the complex OCT data of the entire B-scan 620 of FIG. 6(*a*); and (b) a calculated two-dimensional cross-correlation between the complex OCT data of the entire B-scan 610 and the complex OCT data of the entire B-scan 620 of FIG. 6(*a*).

In process S16 of FIG. 5, a complex cross-correlation between the complex OCT data of the entire first B-scan 610 and the complex OCT data of the entire second B-scan 620 may be calculated by the controller 40. In this case, a peak is observed in the cross-correlation graph, as illustrated in FIG. 7(*a*). There is also a peak in a plot of the calculated two-dimensional cross-correlation, which is shown in FIG. 7(*b*), although this is not clearly visible in FIG. 7(*b*).

However, the inventors have found that phase fluctuations caused by relative movement of the imaging target 30 with respect to the FD-OCT scanner 20 during the scan, which cause the appearance of the bands in FIG. 6(*c*), can degrade the result of the cross-correlation calculation when this is performed using a relatively large first B-scan 610. The inventors have found that, in such cases, it may be advantageous to use only some of the A-scans of the first B-scan 610 in the cross-correlation calculation and, in particularly, to use a predetermined number N A-scans adjacent of the first B-scan 610 (as the third set of samples), where N is selected such that a variation of the phase information among the N A-scans of the first B-scan 610 is less than a predetermined degree of variation.

Figure 8:
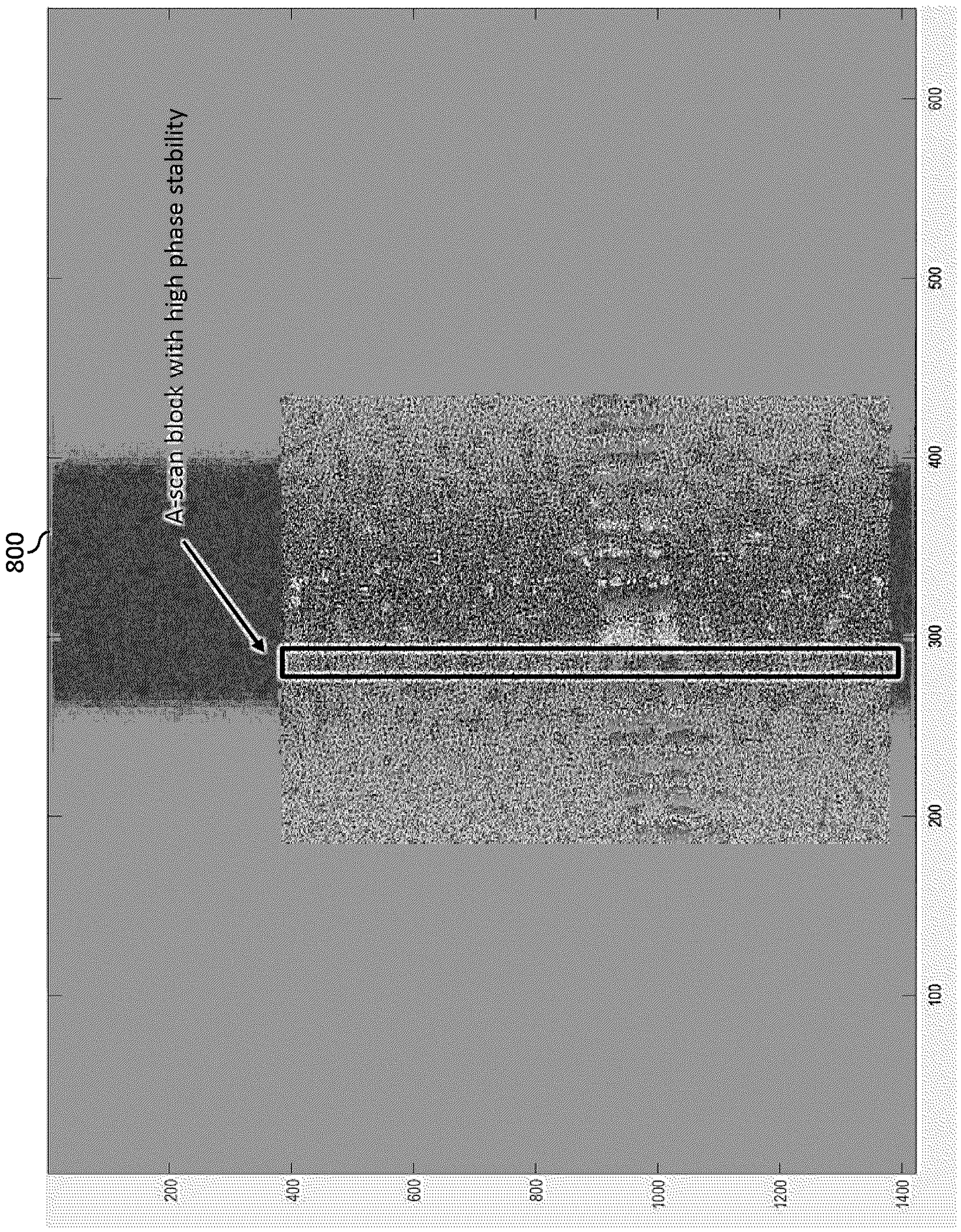
FIG. 8 shows a selected set of adjacent A-scans, which define an A-scan block with high phase stability.

The value of N may be determined in one of several different ways. As one example, N may be determined by calculating a degree of correlation between an i-th A-scan in the first B-scan 610 and the (i+1)-th A-scan in the first B-scan 610, comparing the calculated degree of correlation with a threshold and, if the threshold is exceeded, calculating a degree of correlation between the i-th A-scan and the (i+2)-th A-scan, comparing the calculated degree of correlation with the threshold and, if the threshold is exceeded, calculating a degree of correlation between the i-th A-scan and the next A-scan in the sequence of A-scans that define the first B-scan 610, with this process being repeated (to calculate the correlation between the i-th A-scan and an A-scan that is further away from the i-th A-scan each time the calculation is repeated) until a calculation of a correlation between the i-th A-scan and the (i+N)-th A-scan yields a correlation value that does not exceed the threshold. The value of N may alternatively be obtained from inspection of the difference plot 650 in FIG. 6C, where N may be determined by counting the number of A-scans in a band (e.g. a band of average or minimum width) of the vertical bands that are evident in the plot 650. An example of a set of adjacent A-scans defining an A-scan block 800 with high phase stability is illustrated in FIG. 8.

FIG. 9(*a*) illustrates an example of a set of 10 adjacent A-scans of the first B-scan 610, forming an "OCT strip" (as the third set of samples mentioned above), which has been cross-correlated with the whole of the second B-scan (as the fourth set of samples mentioned above) shown in FIG. 9(*b*) to yield the cross-correlation graph shown in FIG. 9(*c*) and the two-dimensional cross-correlation value plot shown in FIG. 9(*d*). In this example, the cross-correlation is calculated as ifftn(fftn(second B-scan)*conj(fftn(OCT strip))), where "fftn" denotes the fast Fourier transform (FFT), "ifftn" denotes the inverse FFT, and "conj( )" denotes the conjugate. As the enlarged portion of the plot in FIG. 9D shows, there is a clear peak in the calculated two-dimensional cross-correlation.

Figure 9:
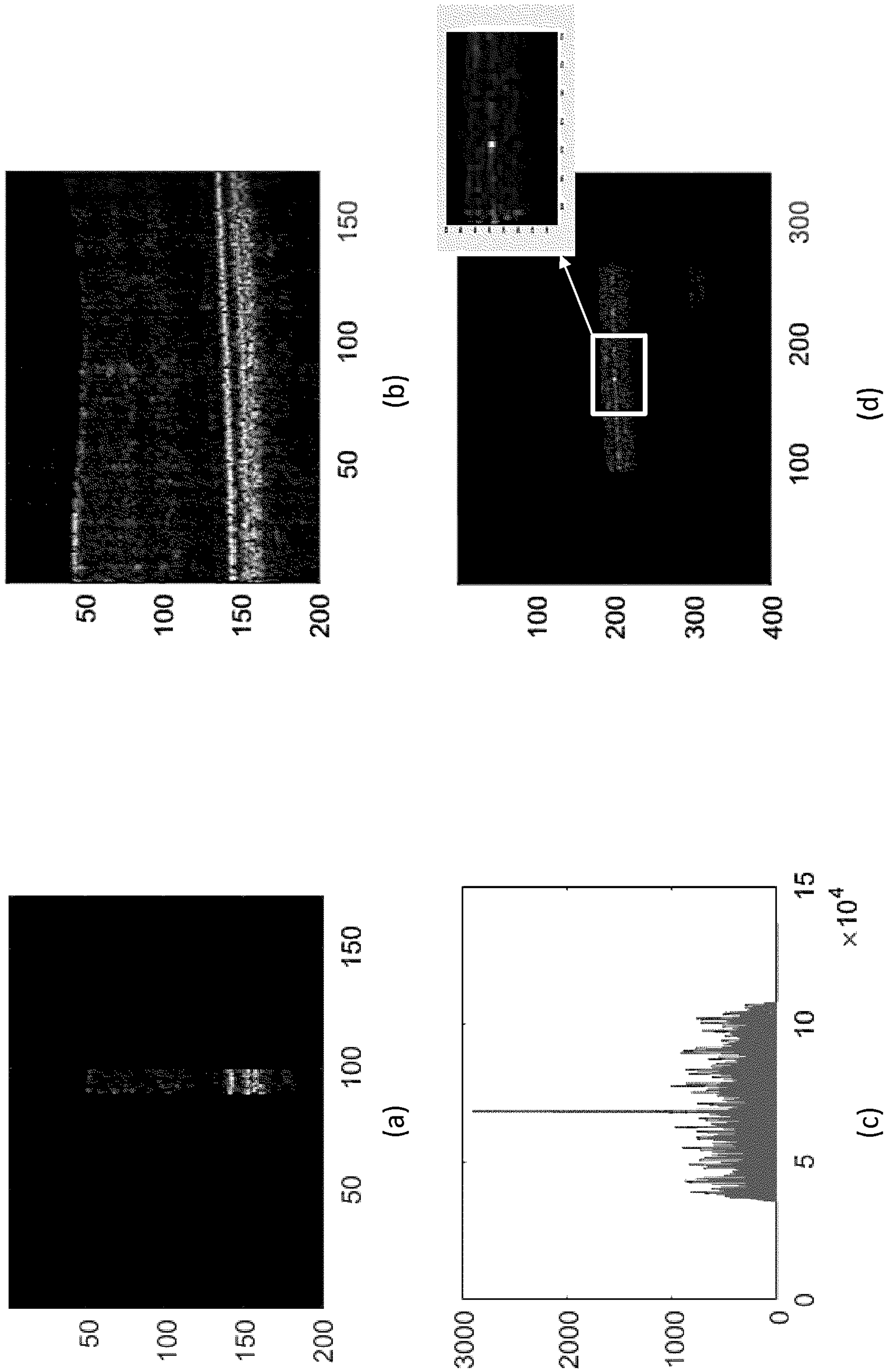
FIG. 9 shows: (a) an example of a set of 10 adjacent A-scans of the B-scan 610 shown in FIG. 6(*a*), which define an A-scan block with high phase stability; (b) the B-scan 620 of FIG. 6(*a*); (c) a cross-correlation graph, which has been obtained by cross-correlating the A-scan block of FIG. 9(*a*) with the B-scan of FIG. 9(*b*); and (d) a two-dimensional cross-correlation value plot, which has been obtained by cross-correlating the A-scan block of FIG. 9(*a*) with the B-scan of FIG. 9(*b*).
Figure 10:
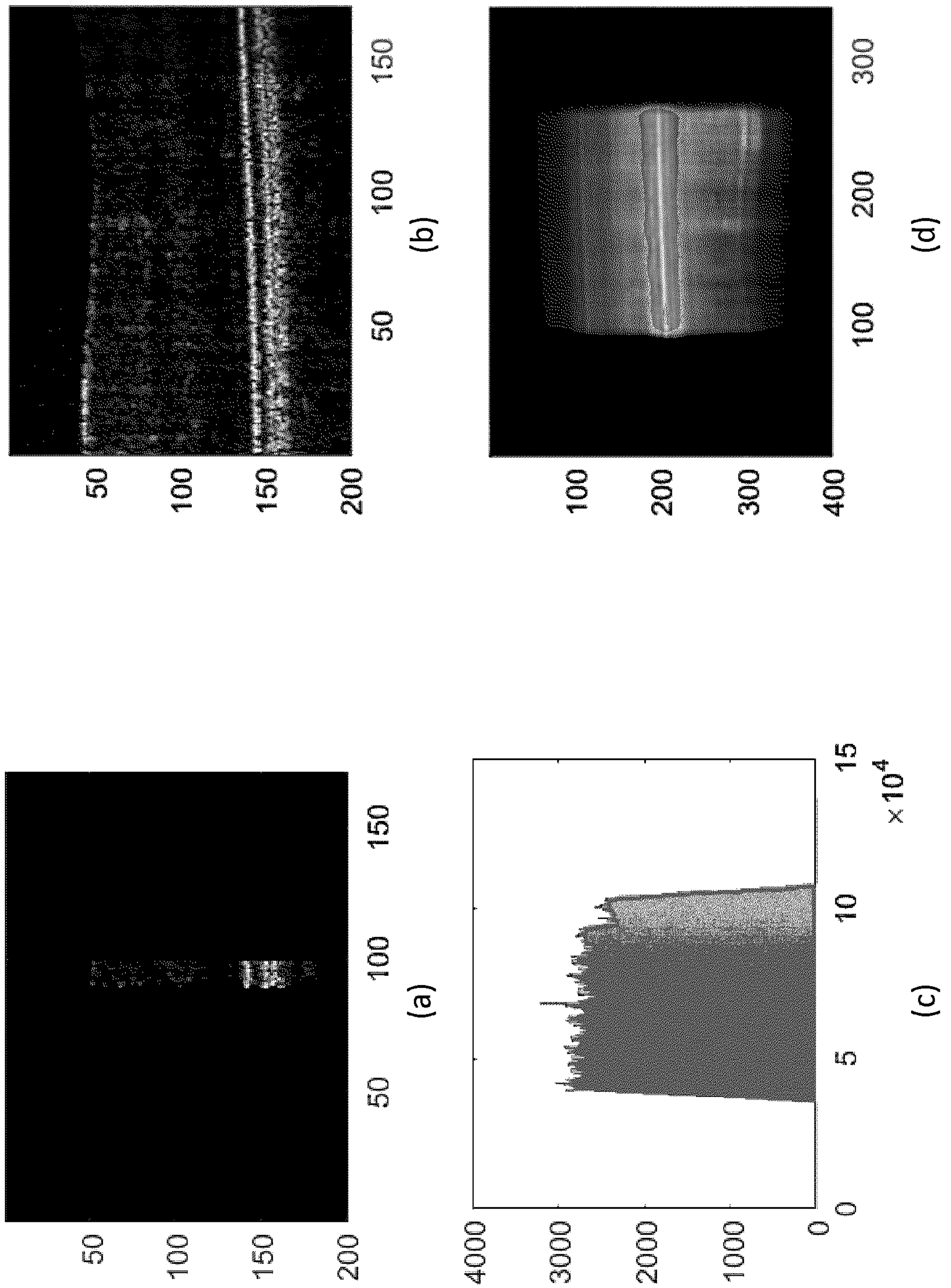
FIG. 10 shows: (a) an example of a set of 10 adjacent A-scans of the B-scan 610 shown in FIG. 6(*a*), which define an A-scan block with high phase stability; (b) the B-scan 620 of FIG. 6(*a*); (c) a cross-correlation graph, which has been obtained by cross-correlating the A-scan block of FIG. 10(*a*) with the B-scan of FIG. 10(*b*); and (d) a two-dimensional cross-correlation value plot, which has been obtained by cross-correlating absolute values of data elements of the A-scan block of FIG. 10(*a*) with absolute values of data elements of the B-scan of FIG. 10(*b*).

For comparison, FIG. 10(*a*) illustrates the same set of 10 adjacent A-scans of the first B-scan 610 as in FIG. 9(*a*), which have been cross-correlated with the whole of the second B-scan shown in FIG. 10(*b*) (which is the same as in FIG. 9(*b*)) to yield the cross-correlation graph shown in FIG. 10(*c*) and the two-dimensional cross-correlation value plot shown in FIG. 10(*d*). However, the cross-correlation calculation in this case does not involve the phase information in the A-scans of FIGS. 10(*a*) and 10(*b*), and is based only on the amplitude of the complex OCT data therein. More specifically, the amplitude-based cross-correlation is calculated as ifftn(fftn(abs(second B-scan))*conj(fftn(abs(OCT strip)))), where "abs( )" is a function which returns the absolute value of the number it operates on. As a result, there is no single peak in either of the plots in FIGS. 10(*c*) and 10(*d*), and the B-scans cannot be registered reliably.

Figure 11:
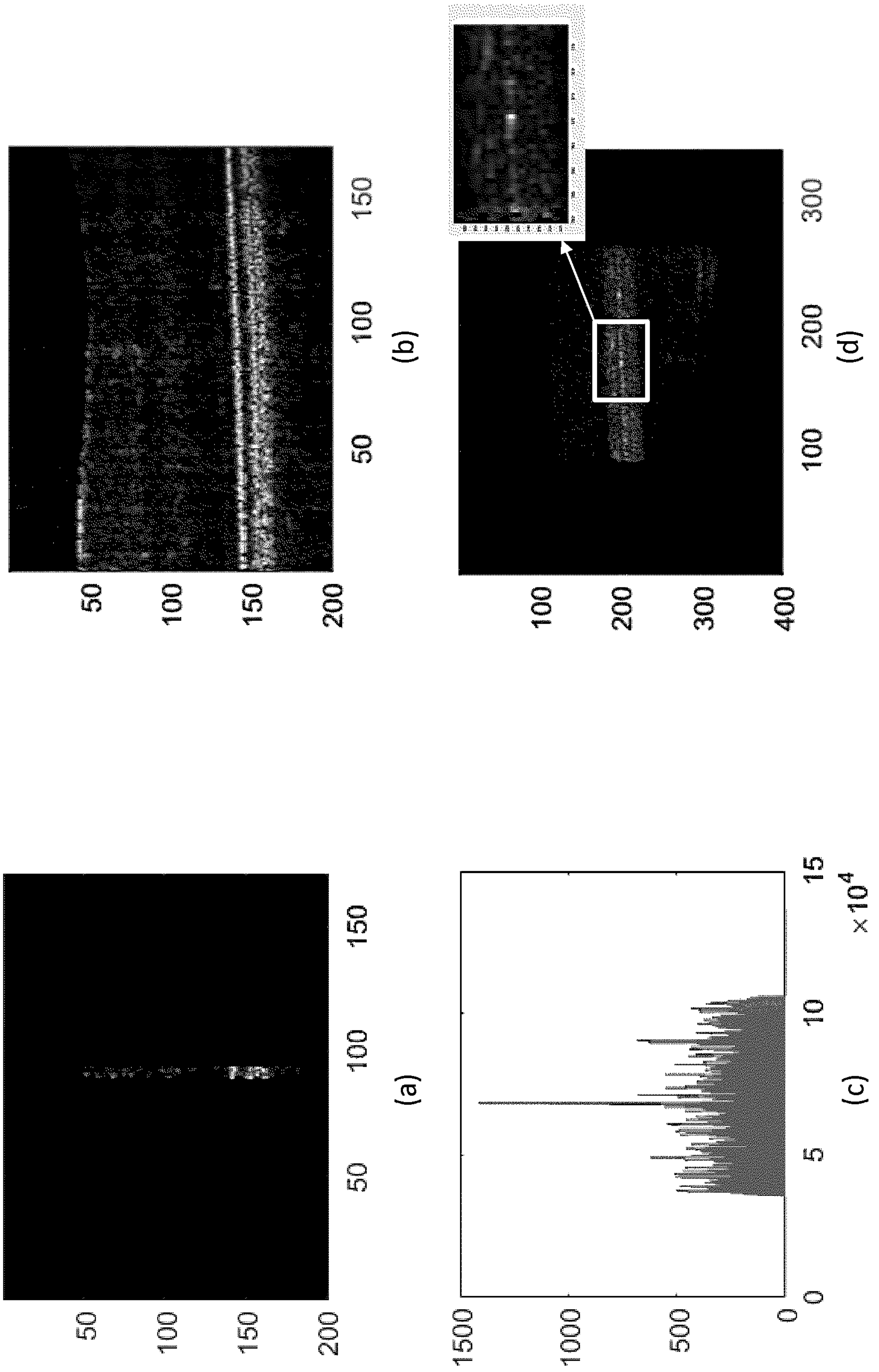
FIG. 11 shows: (a) an example of a set of four adjacent A-scans of the B-scan 610 shown in FIG. 6(*a*), which define an A-scan block with high phase stability; (b) the B-scan 620 of FIG. 6(*a*); (c) a cross-correlation graph, which has been obtained by cross-correlating the A-scan block of FIG. 11 (*a*) with the B-scan of FIG. 11 (*b*); and (d) a two-dimensional cross-correlation value plot, which has been obtained by cross-correlating the A-scan block of FIG. 11 (*a*) with the B-scan of FIG. 11 (*b*).

It should be noted that the OCT strip forming part of the first B-scan 610 need not be composed of 10 A-scans, and may alternatively be composed of a smaller number of adjacent A-scans, across which the phase information of the complex OCT data varies relatively little. By way of an example, the OCT strip of the first B-scan 610 may have four adjacent A-scans, as in the example of FIG. 11(*a*). This smaller set of A-scans (as the third set of samples mentioned above) has been cross-correlated with the whole of the second B-scan (as the fourth set of samples mentioned above) shown in FIG. 11(*b*) to yield the cross-correlation graph shown in FIG. 11(*c*) and the two-dimensional cross-correlation value plot shown in FIG. 11(*d*). As in the example of FIGS. 9(*a*) to 9(*d*), the cross-correlation has been calculated as ifftn(fftn(second B-scan)*conj(fftn(OCT strip))). As the enlarged portion of the plot in FIG. 11(*d*) shows, in the case where N=4, there is once again a single peak in the calculated two-dimensional cross-correlation, despite the OCT strip comprising only four A-scans.

Figure 12:
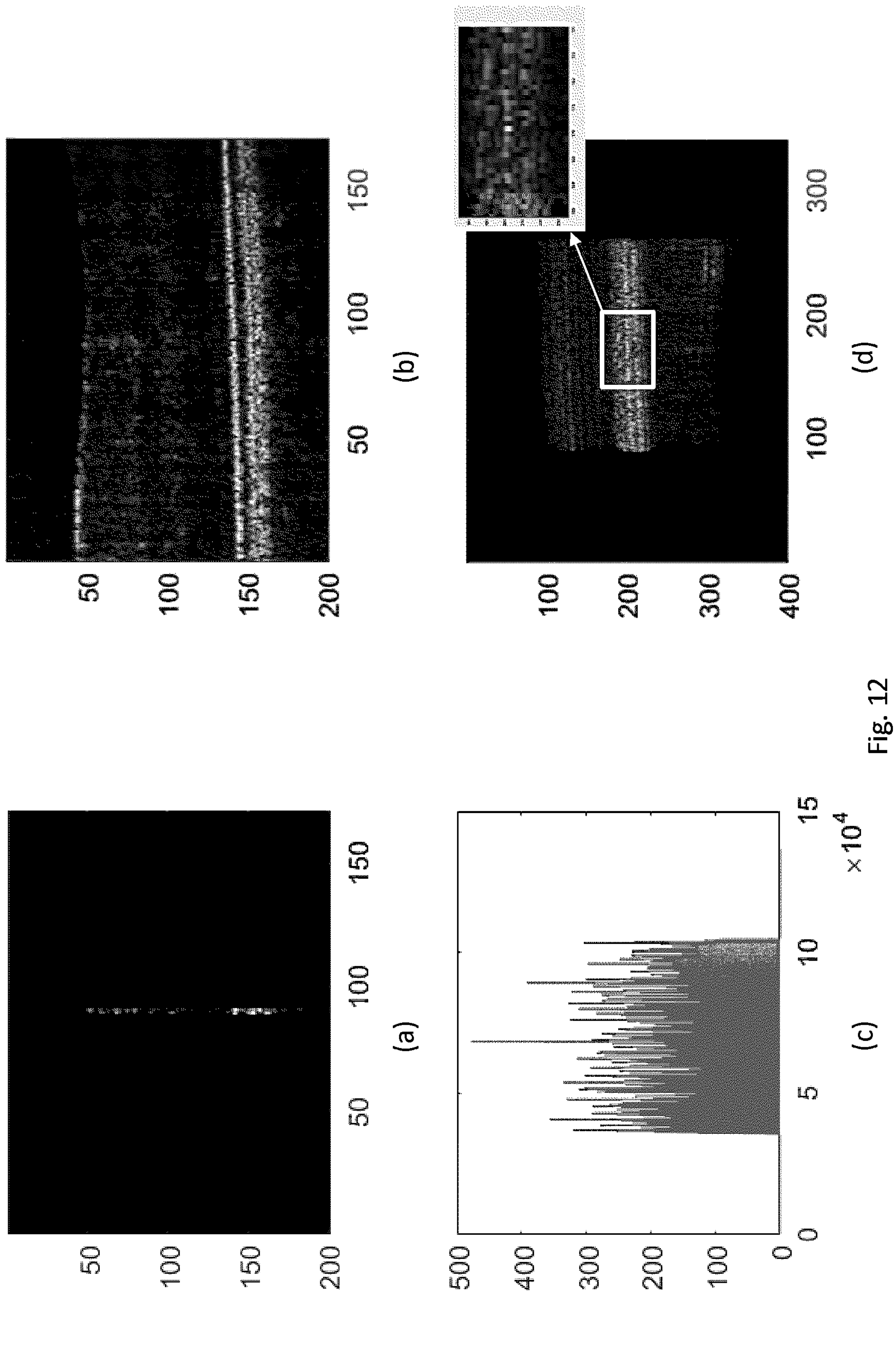
FIG. 12 shows: (a) an example of a set of four adjacent A-scans of the B-scan 610 shown in FIG. 6(*a*), which define an A-scan block with high phase stability; (b) the B-scan 620 of FIG. 6(*a*); (c) a cross-correlation graph, which has been obtained by cross-correlating the A-scan block of FIG. 12(*a*) with the B-scan of FIG. 12(*b*); and (d) a two-dimensional cross-correlation value plot, which has been obtained by cross-correlating the A-scan block of FIG. 12(*a*) with the B-scan of FIG. 12(*b*).

Moreover, an isolated peak in the calculated cross-correlation can be observed even when the number N of A-scans in the OCT strip is reduced to two, as shown in FIGS. 12(*c*) and 12(*d*), which respectively show a cross-correlation graph and a two-dimensional cross-correlation value plot obtained by cross-correlating two adjacent A-scans of the first B-scan 610, as shown in FIG. 12(*a*), with the whole of the second B-scan, as shown in FIG. 12(*b*). As in the example of FIGS. 9(*a*) to 9(*d*), and 11(*a*) to 11(*d*), the cross-correlation has been calculated as ifftn(fftn(second B-scan)*conj(fftn(OCT strip))) in the example of FIGS. 12(*a*) to 12(*d*).

Figure 13:
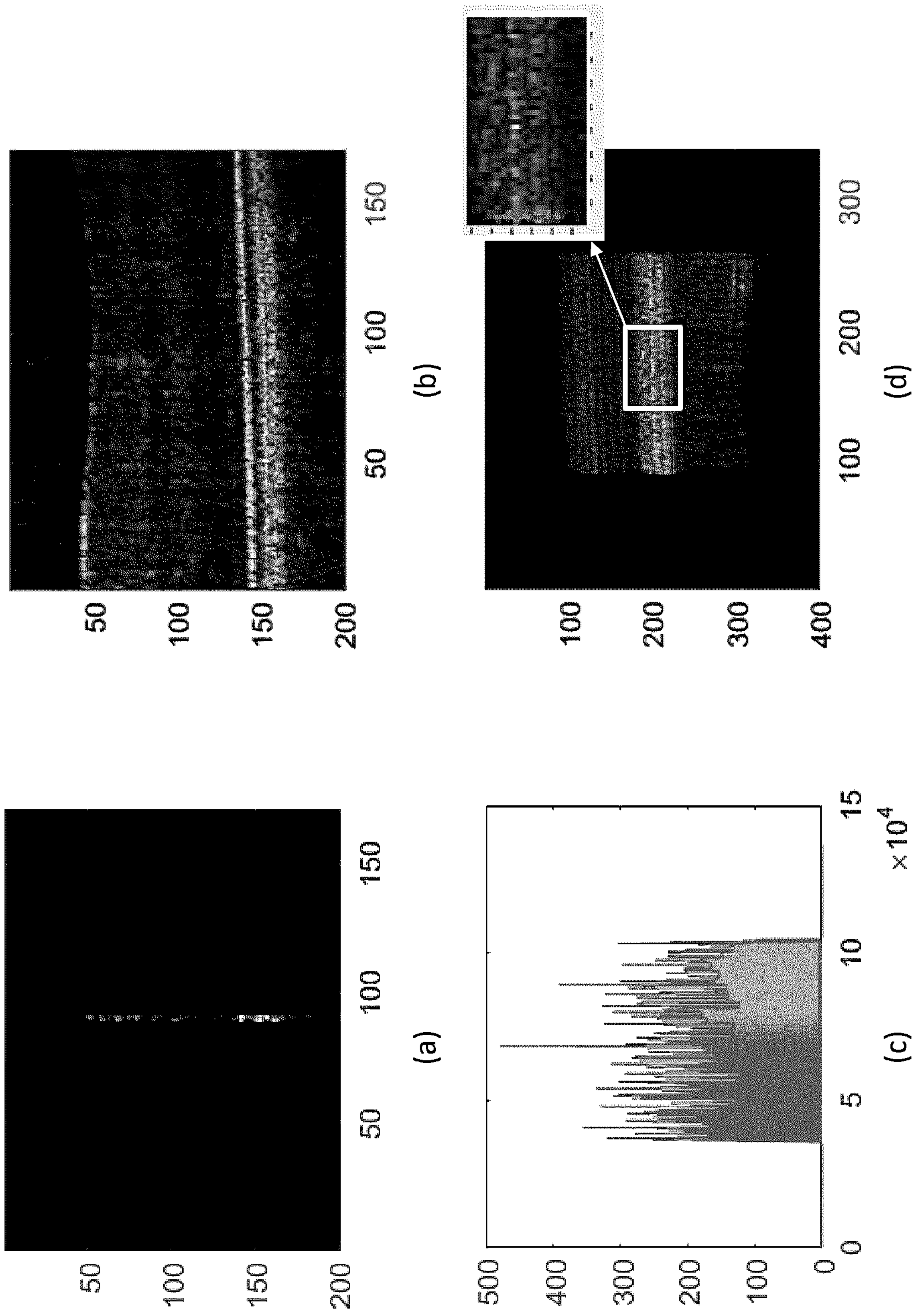
FIG. 13 shows: (a) an example of a single A-scan of the B-scan 610 shown in FIG. 6(*a*), which has been selected for the cross-correlation calculation; (b) the B-scan 620 of FIG. 6(*a*); (c) a cross-correlation graph, which has been obtained by cross-correlating the A-scan of FIG. 13(*a*) with the B-scan of FIG. 13(*b*); and (d) a two-dimensional cross-correlation value plot, which has been obtained by cross-correlating the A-scan of FIG. 13(*a*) with the B-scan of FIG. 13(*b*).

In fact, even a single A-scan (as the OCT strip) can yield an observable peak in the calculated cross-correlation, as shown in FIGS. 13(*c*) and 13(*d*), which respectively show a cross-correlation graph and a two-dimensional cross-correlation value plot obtained by cross-correlating a single A-scan of the first B-scan 610, as shown in FIG. 13(*a*), with the whole of the second B-scan, as shown in FIG. 13(*b*). In this example too, the cross-correlation has been calculated as ifftn(fftn(second B-scan)*conj(fftn(OCT strip))).

Figure 14:
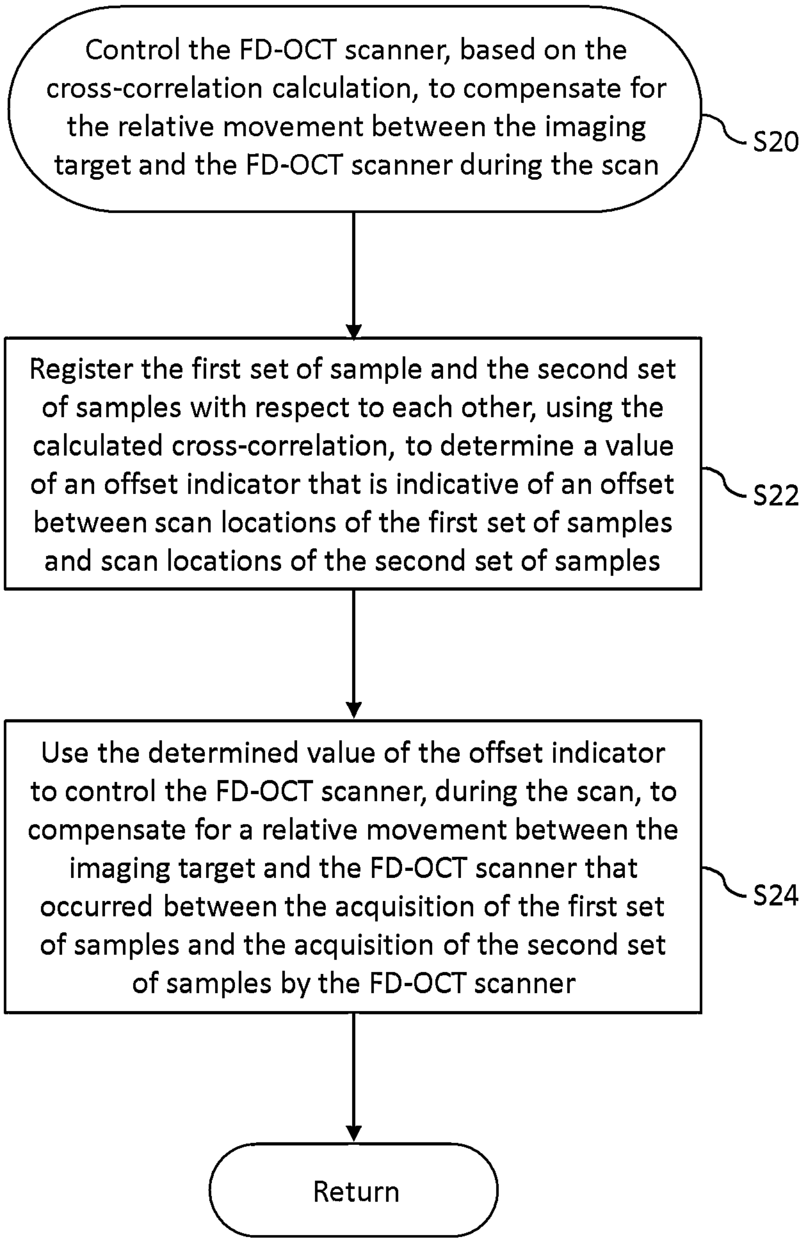
FIG. 14 is a flow diagram illustrating a method by which the FD-OCT scanner may be controlled in process S10 of FIG. 4 to compensate for relative movement between the imaging target and the FD-OCT scanner during a scan being performed thereby.

FIG. 14 is a flow diagram illustrating a process by which the controller 40 may control the FD-OCT scanner 20 to compensate for the relative movement between the imaging target 30 and the FD-OCT scanner 20 in process S20 of FIG. 4.

In process S22 of FIG. 14, the controller 40 registers the first set of samples and the second set of samples with respect to each other, using the calculated cross-correlation, to determine a value of an offset indicator that is indicative of an offset between scan locations of the first set of samples and scan locations of the second set of samples.

In process S22 of FIG. 14, the controller 40 may register the first B-scan 601 (as the first set of samples mentioned above) and the second B-scan 602 (as the second set of samples mentioned above) with respect to each other, by using the calculated cross-correlation to determine, as the value of the offset indicator, an offset value that is indicative of an offset between the first B-scan 601 and the second B-scan 602 in the x-z plane. The controller 40 may perform this registration process by identifying the location of the peak in the calculated two-dimensional cross-correlation, thereby obtaining a coordinate in the x-z plane, from which the value of the offset indicator can be derived.

Where the controller 40 takes only a subset of the A-scans of the first B-scan 610 as the third set of samples for use in the cross-correlation calculation, as described above, the controller 40 may perform a plurality of the cross-correlation calculations in process S22 of FIG. 14 to calculate a respective two-dimensional cross-correlation between each set of a plurality of different sets of N adjacent A-scans of the first B-scan 610 (i.e. each of a plurality of A-scan "chunks", into which the first B-scan 610 is divided) and respective A-scans of the second B-scan 620, where the respective A-scans of the second B-scan 620 include A-scans that are correspondingly located in the second B-scan 620 to the N A-scans in the set (and can therefore be cross-correlated with the N A-scans in the set). Each chunk, n, of a plurality of "OCT chunks" (each chunk being defined by a set of N adjacent A-scans of the first B-scan 610, among which the phase information of the complex OCT data does not vary more than a predetermined amount) may thus be independently cross-correlated with (at least an overlapping portion of) the second B-scan 620 to obtain a respective cross-correlation, $C_{A\text{-}scan\ chunk,n}$ (x, y). The controller 40 may calculate a combined cross-correlation, $C_{B\text{-}scan}$ (x, y), for registering the first B-scan 610 with respect to the second B-scan 620, by calculating a sum of the magnitudes of the independently calculated cross-correlations, $C_{A\text{-}scan\ chunk,n}$ (x, y), as follows:

$$C_{B\text{-}scan}(x, y) = \sum_{n=1}^{N} |C_{A\text{-}scan\ chunk,n}(x, y)|$$

Although smaller OCT chunks tend to be affected relatively little by motion, the advantages of using small OCT chunks (each of which may be as small as a single A-scan) need to be weighed against the increased processing burden on the controller 40 that their processing causes. The controller 40 may then determine, as an overall offset value (or "combined offset value"), a value that is indicative of an offset between the first B-scan 610 and the second B-scan 620, on the basis of $C_{B\text{-}scan}$ (x, y).

In process S24 of FIG. 14, the controller uses the value of the offset indicator determined in S22 to control the FD-OCT scanner 20, during the scan, to compensate for a relative movement between the imaging target 30 and the FD-OCT scanner 20 that occurred between the acquisition of the first B-scan 601 (as an example of the first set of samples in the present embodiment) and the acquisition of the second B-scan (as an example of the second set of samples in the present embodiment) by the FD-OCT scanner 20.

Where the controller 40 performs a plurality of the cross-correlation calculations in process S22 of FIG. 14 to calculate a respective two-dimensional cross-correlation between each set of a plurality of different sets of N adjacent A-scans of the first B-scan 610 ("OCT chunks") and respective A-scans of the second B-scan 620, as described above, the controller 40 may control the FD-OCT scanner 20 in process S24 of FIG. 14 to compensate for the relative movement between the imaging target 30 and the FD-OCT scanner 20 by using the determined overall (or combined) offset value mentioned above, which is indicative of the offset between the first B-scan 610 and the second B-scan 620.

In process S24, the controller 40 uses the determined value of the offset indicator (or the combination of determined values of the offset indicator described above, as the case may be) to modify the scan being performed by the FD-OCT scanner 20 so that, after the modification of the scan, the remainder of the scan (comprising the acquisition or one or more repeat B-scans) is performed with there being no effect, or a reduced effect, of the prior relative movement on samples acquired by the FD-OCT scanner 20 on the remainder of the scan (as compared to the case where the modification of the scan is not performed).

Second Example Embodiment

In the first example embodiment described above, the FD-OCT scanner 20 is arranged to generate the complex OCT data 25 by performing, as the scan, repeat linear scans of the light beam $L_b$ over the imaging target 30 along overlapping scan lines on the imaging target 30, such that the acquired samples define repeat B-scans representing respective images of a common cross-section of the imaging target 30. However, as noted above, the FD-OCT scanner 20 may alternatively generate the complex OCT data 25, on which the motion compensation is based, in other ways.

The FD-OCT scanner 20 may, as in the present example embodiment, be arranged to generate the complex OCT data 25 by performing, as the scan, an area OCT scan of the imaging target 30, to acquire samples having complex values that are indicative of the optical property of the imaging target 30 at respective scan locations that are distributed three-dimensionally in the imaging target 30. The FD-OCT scanner 20 may perform such an area OCT scan in various different ways.

Figure 15:
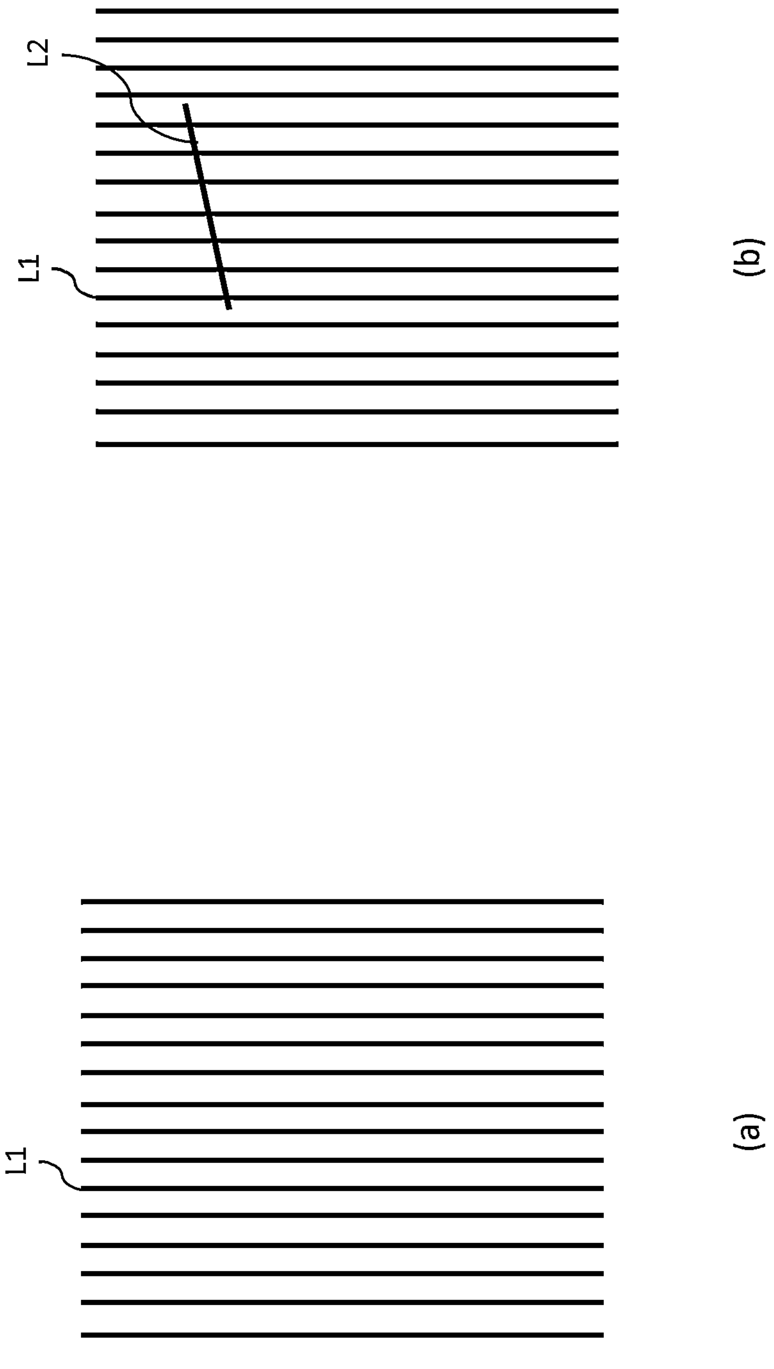
FIG. 15 illustrates: (a) a reference grid of raster scans defined by parallel scan lines; and (b) a second scan line (L2) crossing a first scan line (L1), which forms one of the parallel scan lines defining the reference grid of raster scans.

By way of an example, the first scan line mentioned above may be one of a plurality of parallel scan lines on the imaging target 30, along which parallel scan lines the FD-OCT scanner 20 of the present example embodiment is arranged to scan the light beam $L_b$ and thus acquire an OCT C-scan as the complex OCT data 25. These parallel scan lines define a reference grid of raster scans, which collectively form a reference scan, as illustrated in FIG. 15(*a*). The reference grid is preferably sparse enough for the raster scans to be performed quickly (so that the reference scan is substantially motion-free at a typical saccade rate) but not so sparse that the reference scan has inadequate density to allow the registration process described herein below to be performed reliably. The size (lateral extent) of the reference scan preferably covers the imaged region of interest on the ocular fundus, plus the maximum likely motion so that the scan position on the fundus can be tracked by the FD-OCT scanner 20 even if it moves away from the imaged region.

As illustrated in FIG. 15(*b*), the second scan line mentioned above crosses the first scan line at a point on the surface of the imaging target 30, and may (as in the example of FIG. 15(*b*)) cross one or more additional ones of the parallel scan lines at respective one or more crossing points. In FIG. 15(*b*), the scan line identified with the first scan line mentioned above is labelled "L1", and the scan line identified with the second scan line mentioned above is labelled "L2". Scan lines L1 and L2 are followed by the light beam $L_b$ to acquire samples from different scan locations on the imaging target 30, including a common region of the imaging target 30, where the scan lines L1 and L2 intersect each other. It is noted that scan line L2 may be one of a set of parallel scan lines, along which the FD-OCT scanner 20 is arranged to scan the light beam $L_b$ to acquire a C-scan of the imaging target 30.

Figure 16:
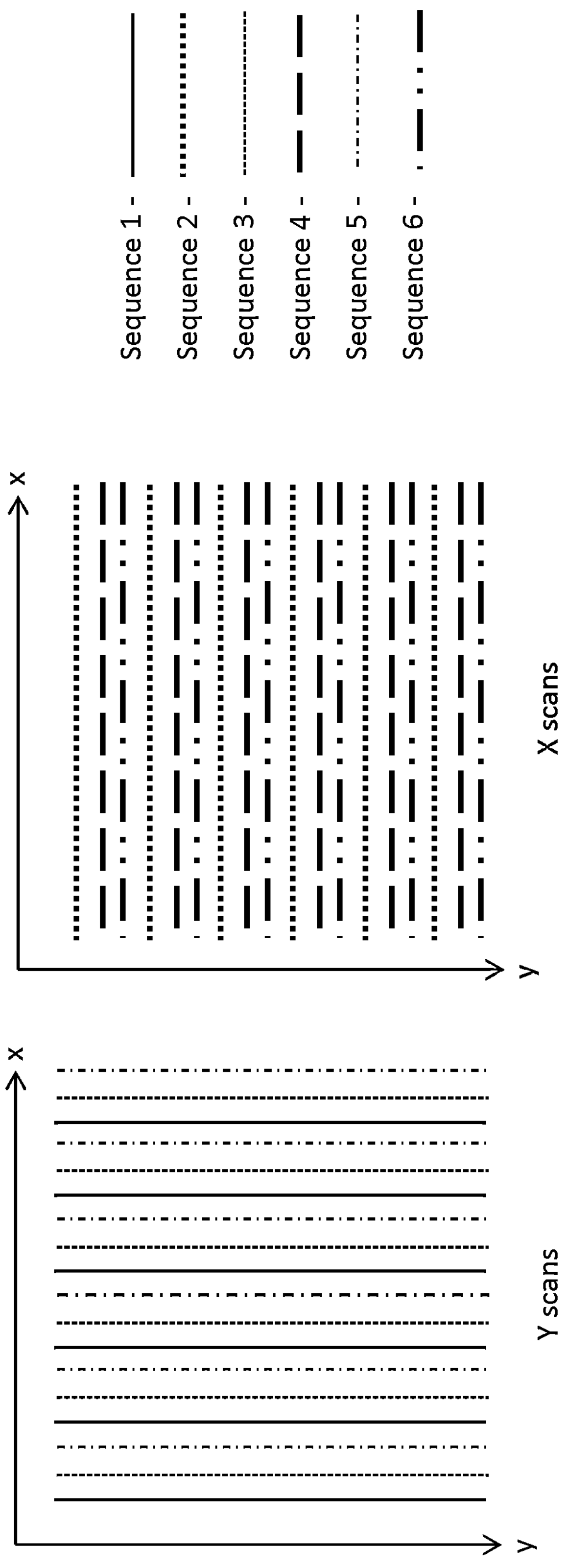
FIG. 16 illustrates a sequence in which a FD-OCT scanner of an example embodiment may scan an OCT light beam along vertical and horizontal scan lines to acquire a volumetric OCT scan of an imaged region of an imaging target.

Although the reference scan, comprising the first scan line L1 and the scan lines parallel to the first scan line L1, may be completed by the FD-OCT scanner 20 before the FD-OCT scanner 20 starts performing a measurement scan to acquire a C-scan comprising complex OCT data acquired from scanning along the second scan line L2 and further scan lines parallel to the second scan line L2, with eye movements during the measurement scan being compensated for by the controller 40 by the techniques described herein using the complex OCT data of the reference scan, it is noted that the scanning scheme employed by the FD-OCT scanner 20 is not so limited. For example, the FD-OCT scanner 20 may alternatively acquire the reference scan and the measurement scan concurrently, alternating between performing component horizontal and vertical line scans, and using the techniques described herein to register OCT data acquired in each horizontal scan with OCT data acquired in the preceding vertical scan to acquire an offset for correcting the scan location of the next horizontal scan, for example. An example of a sequence, in which the horizontal and vertical line scans are alternatively performed, is illustrated in FIG. 16. In the example of FIG. 16, a set of vertical (Y) scans, which is labelled as "Sequence 1", is performed first, followed by a set of horizontal (X) scans, which is labelled as "Sequence 2", then followed by another set of vertical (Y) scans, which is labelled as "Sequence 3" and displaced along the x-axis with respect to the vertical scans of "Sequence 1", etc. It should be noted that the FD-OCT scanner 20 may scan along each of the horizontal and/or vertical scan lines shown in FIG. 16 more than once, for example where the FD-OCT scanner 20 is being used to acquire OCT data for OCT angiography (OCTA).

Figure 17:
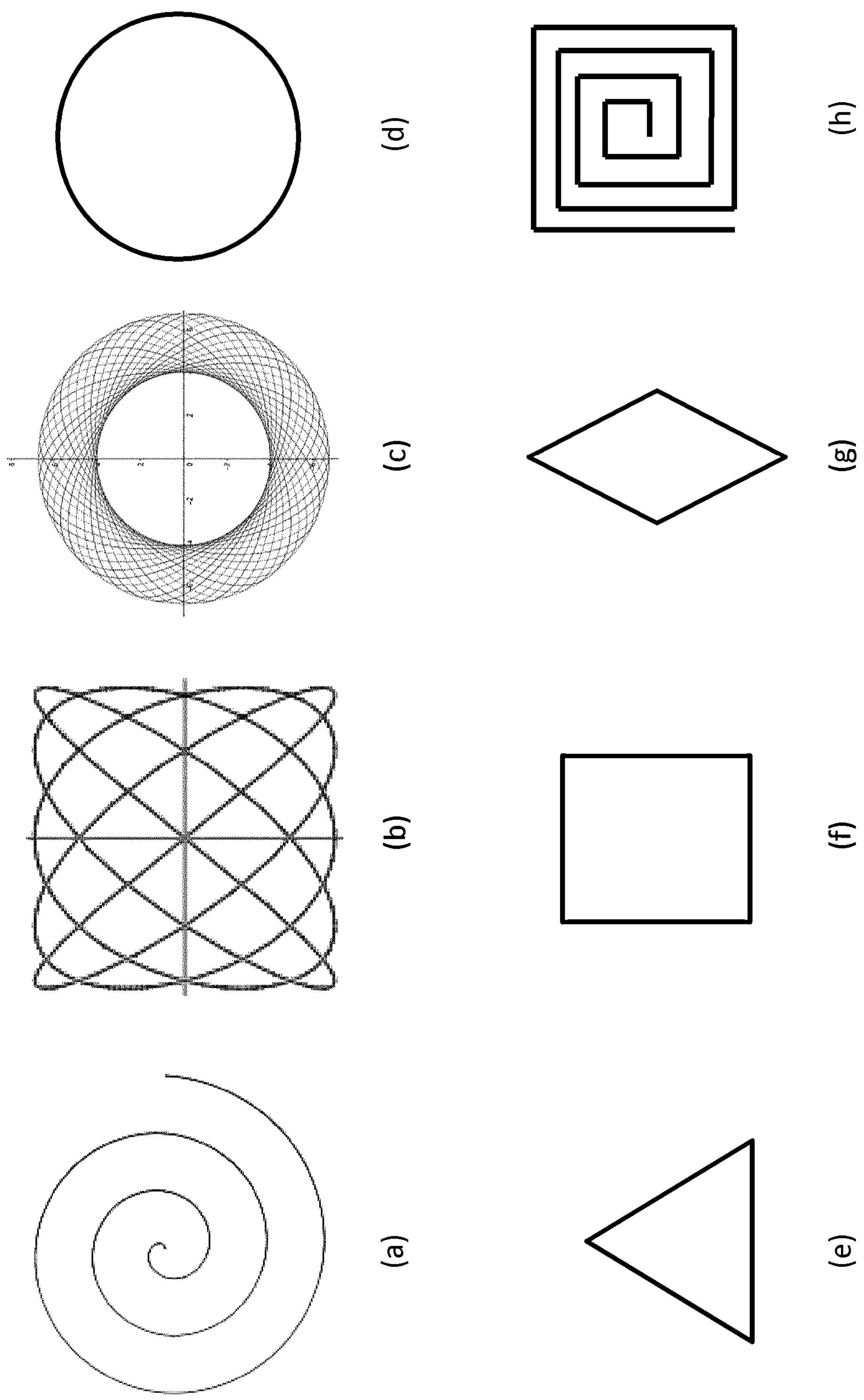
FIG. 17 illustrates example sparse reference scans in the form of: (a) a spiral; (b) a Lissajous figure; (c) an epitrochoid/hypotrochoid; (d) a circle (as an example of an ellipse); (e) a triangle; (f) a square; (g) a diamond; and (h) a square spiral.

It should also be noted that the first scan line, which is referred to in the description of the first example embodiment, need not be straight and may be curved so as to extend along two dimensions on the surface of imaging target and define a "sparse" reference scan, as an alternative to the scans discussed above with reference to FIGS. 15(*a*), 15(*b*) and 16. The sparse reference scan defined by the first scan line may, for example, define a spiral (as illustrated in FIG. 17(*a*)), a Lissajous figure (as illustrated in FIG. 17(*b*)), an epitrochoid or a hypotrochoid (as illustrated in FIG. 17(*c*)), a circle (as illustrated in FIG. 17(*d*)), a triangle (as illustrated in FIG. 17(*e*)), a square (as illustrated in FIG. 17(*f*)), a diamond (as illustrated in FIG. 17(*g*)), a square (as illustrated in FIG. 17(*h*)) or an ellipse on the imaging target 30. The reference scans illustrated in FIGS. 17(*a*) to 17(*h*) are given by way of example only, and the first scan line may define many other shapes that extend over the surface of the imaging target 30. Whichever form the first scan line takes, the second scan line is arranged to cross it at at least one point so that the complex OCT data from at least one common region of the imaging target 30 (where the two scan lines cross) is acquired from scanning along the scan lines.

It should also be noted that the first scan line and the second scan line need not be different line segments, and may alternatively be different respective parts of a single, continuous scan line (line segment), which extends along two dimensions on the imaging target 30 and intersects itself. In this case, the single scan line may define a Lissajous figure, an epitrochoid or a hypotrochoid on the imaging target 30, for example. The single scan line may more generally be any type of scan line which self-intersects as it extends over the measurement area on the fundus to cover scan locations not previously covered by the scan (with the scan locations eventually covered being sufficiently dense to provide the required OCT scan). This scanning scheme could be combined with the use of a previously acquired sparse reference scan, as described above, to increase the motion correction capability beyond the measurement area.

In the present example embodiment, the controller 40 is arranged to acquire for the cross-correlation calculation described above, as the first set of samples, a set of samples comprising samples which have been acquired by the FD-OCT scanner 20 scanning the imaging target 30 along the first scan line, as at least a part of the area OCT scan.

Where the first scan line is one of the plurality of parallel scan lines on the imaging target 30 mentioned above, the controller 40 may be arranged to acquire, as the first set of samples, the complex OCT data of the whole C-scan. Where the first scan line takes one of the alternative forms set out above, the controller 40 may acquire, as the first set of samples, the complex OCT data of the first scan line of the respective form.

The controller 40 may then calculate the complex cross-correlation between the acquired sets of samples based on a masked intensity cross-correlation.

The masked cross-correlation, without normalization, may be expressed as:

$$MC(u, v, w) = \sum_{x,y,z} f_1(x, y, z)M_1(x, y, z)f_2^*(x-u, y-v, z-w)M_2(x-u, y-v, z-w)$$

The masked cross-correlation, normalized using signal RMS, may be expressed as:

$$MCN(u, v, w) = \frac{\sum_{x,y,z} f_1(x, y, z)M_1(x, y, z)\, f_2^*(x-u, y-v, z-w)M_2(x-u, y-v, z-w)}{\sqrt{\sum_{x,y,z} |f_1(x, y, z)|^2 M_1(x, y, z)M_2(x-u, y-v, z-w)}\ \sqrt{\sum_{x,y,z} |f_2(x-u, y-v, z-w)|^2 M_1(x, y, z)M_2(x-u, y-v, z-w)}}$$

In the above expression, the average does not need to be normalized as complex signals tend to have an average or zero.

In the above expressions for MC(u, v, w) and MCN (u, v, w), $$M_1(x, y, z) = \begin{matrix} 1 & \text{for the region where function } f_1(x, y, z) \text{ is defined,} \\ 0 & \text{otherwise} \end{matrix}$$

$$M_2(x, y, z) = \begin{matrix} 1 & \text{for the region where function } f_1(x, y, z) \text{ is defined,} \\ 0 & \text{otherwise} \end{matrix}$$

As an alternative to the masked cross-correlation described above, the regions may be divided in smaller sub-regions, for example where the function $f_1$ or $f_2$ keeps coherence (where the phase of the complex OCT data is not affected by motion). Otherwise, the complex cross-correlation affected by random motion phase would average out to zero in the final result, due to destructive interference.

Subregions can be defined for just one of the functions $f_1$ and $f_2$ or for both of them in the most general way. Each sub-correlation for a subregion can be computed similarly as in the previous expressions, and then summed in absolute value.

$$M_{1,i}(x, y, z) = \begin{matrix} 1 & \text{for the subregion } i \text{ of complex function } f_1(x, y, z), \\ 0 & \text{otherwise} \end{matrix}$$

$$M_{2,j}(x, y, z) = \begin{matrix} 1 & \text{for the subregion } j \text{ of complex function } f_2(x, y, z), \\ 0 & \text{otherwise} \end{matrix}$$

The masked cross-correlation, without normalization, may be expressed as:

$$MC(u, v, w) = \sum_{i,j} \left| \sum_{x,y,z} f_1(x, y, z)M_{1,i}(x, y, z)f_2^*(x-u, y-v, z-w)M_{2,j}(x-u, y-v, z-w) \right|$$

The masked cross-correlation, normalized using signal RMS, may be expressed as:

$$MCN(u, v, w) = \sum_{i,j} \frac{\left| \sum_{x,y,z} f_1(x, y, z)M_{1,i}(x, y, z)f_2^*(x-u, y-v, z-w)M_{2,j}(x-u, y-v, z-w) \right|}{\sqrt{\sum_{x,y,z} |f_1(x, y, z)|^2 M_{1,i}(x, y, z)M_{2,j}(x-u, y-v, z-w)}\ \sqrt{\sum_{x,y,z} |f_2(x-u, y-v, z-w)|^2 M_{1,i}(x, y, z)M_{2,j}(x-u, y-v, z-w)}}$$

Coherent regions are defined as regions where the phase of complex function $f_1(x,y,z)$ is not affected significantly by motion artefacts. This condition is much more restrictive than just a distortion of the shape but it implies that the motion should be significantly smaller than the central wavelength of the OCT laser.

The maximum of the cross-correlation MC(u,v,w) or MCN(u,v,w) can be found by the controller 40, and indicates the most likely position of a scan line defined by function $f_2$ in a reference scan that is defined by function $f_1$. Scan positions determined in this way, based on calculated complex cross-correlations between complex OCT data acquired from each line scan of a set of sequentially-performed line scans and the reference scan, may be used by the controller 40, together with information on the spatial distribution of the sequentially-performed line scans, to move one or more galvanometers ("galvos") or other scanning element(s) of the FD-OCT scanner 20 in real time, so as to compensate for relative movement of the imaging target 30 and the FD-OCT scanner 20 during the performance of the line scans. In particular, the controller 40 may use the aforementioned information and the determined scan positions to calculate offsets between expected scan positions and the determined scan positions, and control the FD-OCT scanner 20 based on the calculated offsets to compensate for the relative movement of the imaging target 30 and the FD-OCT scanner 20 during the scan. It is noted that the result of the complex cross-correlation calculation may be used by the controller 40 of the present example embodiment to compensate not only for relative movement of the imaging target 30 and the FD-OCT scanner 20 in a plane normal to the direction of the OCT light beam $L_b$ used to acquire the complex OCT data 25 but also for movements along an axis along which the OCT light beam $L_b$ travels during the scan.

In the foregoing description, example aspects are described with reference to several example embodiments. Accordingly, the specification should be regarded as illustrative, rather than restrictive. Similarly, the figures illustrated in the drawings, which highlight the functionality and advantages of the example embodiments, are presented for example purposes only. The architecture of the example embodiments is sufficiently flexible and configurable, such that it may be utilized in ways other than those shown in the accompanying figures.

Some aspects of the examples presented herein, such as the processing of the detection signal $S_d$ to generate complex volumetric OCT data of the imaging target 140, and the correction algorithm 132, may be provided as a computer program, or software, such as one or more programs having instructions or sequences of instructions, included or stored in an article of manufacture such as a machine-accessible or machine-readable medium, an instruction store, or computer-readable storage device, each of which can be non-transitory, in one example embodiment. The program or instructions on the non-transitory machine-accessible medium, machine-readable medium, instruction store, or computer-readable storage device, may be used to program a computer system or other electronic device. The machine- or computer-readable medium, instruction store, and storage device may include, but are not limited to, floppy diskettes, optical disks, and magneto-optical disks or other types of media/machine-readable medium/instruction store/storage device suitable for storing or transmitting electronic instructions. The techniques described herein are not limited to any particular software configuration. They may find applicability in any computing or processing environment. The terms "computer-readable", "machine-accessible medium", "machine-readable medium", "instruction store", and "computer-readable storage device" used herein shall include any medium that is capable of storing, encoding, or transmitting instructions or a sequence of instructions for execution by the machine, computer, or computer processor and that causes the machine/computer/computer processor to perform any one of the methods described herein. Furthermore, it is common in the art to speak of software, in one form or another (e.g., program, procedure, process, application, module, unit, logic, and so on), as taking an action or causing a result. Such expressions are merely a shorthand way of stating that the execution of the software by a processing system causes the processor to perform an action to produce a result.

Some or all of the functionality of the OCT data processing hardware 130 may also be implemented by the preparation of application-specific integrated circuits, field-programmable gate arrays, or by interconnecting an appropriate network of conventional component circuits.

A computer program product may be provided in the form of a storage medium or media, instruction store(s), or storage device(s), having instructions stored thereon or therein which can be used to control, or cause, a computer or computer processor to perform any of the procedures of the example embodiments described herein. The storage medium/instruction store/storage device may include, by example and without limitation, an optical disc, a ROM, a RAM, an EPROM, an EEPROM, a DRAM, a VRAM, a flash memory, a flash card, a magnetic card, an optical card, nanosystems, a molecular memory integrated circuit, a RAID, remote data storage/archive/warehousing, and/or any other type of device suitable for storing instructions and/or data.

Stored on any one of the computer-readable medium or media, instruction store(s), or storage device(s), some implementations include software for controlling both the hardware of the system and for enabling the system or microprocessor to interact with a human user or other mechanism utilizing the results of the example embodiments described herein. Such software may include without limitation device drivers, operating systems, and user applications. Ultimately, such computer-readable media or storage device(s) further include software for performing example aspects of the invention, as described above.

Included in the programming and/or software of the system are software modules for implementing the procedures described herein. In some example embodiments herein, a module includes software, although in other example embodiments herein, a module includes hardware, or a combination of hardware and software.

While various example embodiments of the present invention have been described above, it should be understood that they have been presented by way of example, and not limitation. It will be apparent to persons skilled in the relevant art(s) that various changes in form and detail can be made therein. Thus, the present invention should not be limited by any of the above-described example embodiments, but should be defined only in accordance with the following claims and their equivalents.

Further, the purpose of the Abstract is to enable the Patent Office and the public generally, and especially the scientists, engineers and practitioners in the art who are not familiar with patent or legal terms or phraseology, to determine quickly from a cursory inspection the nature and essence of the technical disclosure of the application. The Abstract is not intended to be limiting as to the scope of the example embodiments presented herein in any way. It is also to be understood that any procedures recited in the claims need not be performed in the order presented.

While this specification contains many specific embodiment details, these should not be construed as limitations on the scope of any inventions or of what may be claimed, but rather as descriptions of features specific to particular embodiments described herein. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

In certain circumstances, multitasking and parallel processing may be advantageous. Moreover, the separation of various components in the embodiments described above should not be understood as requiring such separation in all embodiments, and it should be understood that the described program components and systems can generally be integrated together in a single software product or packaged into multiple software products.

Having now described some illustrative embodiments and embodiments, it is apparent that the foregoing is illustrative and not limiting, having been presented by way of example. In particular, although many of the examples presented herein involve specific combinations of apparatus or software elements, those elements may be combined in other ways to accomplish the same objectives. Acts, elements and features discussed only in connection with one embodiment are not intended to be excluded from a similar role in other embodiments or embodiments.

The invention claimed is:

1. A Fourier-domain optical coherence tomography, FD-OCT, imaging system, comprising:

an FD-OCT scanner arranged to generate complex OCT data by performing a scan of an imaging target to acquire samples whose complex values are indicative of an optical property of the imaging target at respective scan locations in the imaging target, the FD-OCT scanner comprising a scanning system arranged to perform a scan of a light beam across the imaging target and collect light that has been scattered by the imaging target during the scan; and a controller arranged to perform a cross-correlation calculation that uses phase information of the acquired samples, and control the scanning system of the FD-OCT scanner, based on the cross-correlation calculation, to compensate for a relative movement between the imaging target and the FD-OCT scanner during the scan.

2. The Fourier-domain OCT imaging system according to claim 1, wherein the controller is arranged to:

perform the cross-correlation calculation by:

acquiring a first set of the samples, the samples of the first set comprising samples that have been acquired by the FD-OCT scanner scanning the imaging target along a first scan line on the imaging target;

acquiring a second set of the samples, the samples of the second set comprising samples that have been acquired by the FD-OCT scanner scanning the imaging target along a second scan line on the imaging target, wherein the second scan line at least partially overlaps the first scan line; and performing the cross-correlation calculation to calculate a cross-correlation between a third set of samples comprising at least some samples of the first set of samples, and a fourth set of samples comprising at least some samples of the second set of samples, at least some samples of the third set of samples and at least some samples of the fourth set of samples having been acquired from a common region of the imaging target at which the first scan line and the second scan line overlap, the cross-correlation calculation being based on phase information in the third set of samples and phase information in the fourth set of samples, and control the FD-OCT scanner to compensate for the relative movement between the imaging target and the FD-OCT scanner during the scan by:

registering the first set of samples and the second set of samples with respect to each other using the calculated cross-correlation to determine a value of an offset indicator that is indicative of an offset between scan locations of the first set of samples and scan locations of the second set of samples; and using the determined value of the offset indicator to control the FD-OCT scanner, during the scan, to compensate for a relative movement between the imaging target and the FD-OCT scanner that occurred between the acquisition of the first set of samples and the acquisition of the second set of samples by the FD-OCT scanner.

3. The Fourier-domain OCT imaging system according to claim 2, wherein:

the FD-OCT scanner is arranged to generate the complex OCT data by performing, as the scan, repeat linear scans of the imaging target along overlapping scan lines on the imaging target, such that the acquired samples define repeat B-scans of the imaging target, and the controller is arranged to:

perform the cross-correlation calculation by:

acquiring, as the first set of the samples, a first B-scan of the repeat B-scans;

acquiring, as the second set of the samples, a second B-scan of the repeat B-scans; and performing, as the cross-correlation calculation, a cross-correlation calculation to calculate a two-dimensional cross-correlation between one or more A-scans of the first B-scan, and A-scans of the second B-scan, wherein the A-scans of the second B-scan include A-scans that are correspondingly located in the second B-scan to the one or more A-scans in the first B-scan, and control the FD-OCT scanner to compensate for the relative movement between the imaging target and the FD-OCT scanner during the scan by:

registering the first B-scan, as the first set of samples, and the second B-scan, as the second set of samples, with respect to each other, by using the calculated cross-correlation to determine, as the value of the offset indicator, an offset value that is indicative of an offset between the first B-scan and the second B-scan; and controlling the FD-OCT scanner to compensate for a relative movement between the imaging target and the FD-OCT scanner that occurred between the acquisition of the first B-scan and the acquisition of the second B-scan by the FD-OCT scanner, by using the determined offset value.

4. The Fourier-domain OCT imaging system according to claim 3, wherein the controller is arranged to perform, as the cross-correlation calculation, a cross-correlation calculation to calculate a two-dimensional cross-correlation between a predetermined number of A-scans of the first B-scan, and A-scans of the second B-scan, the cross-correlation calculation being based on phase information in the predetermined number of A-scans of the first B-scan and phase information in the A-scans of the second B-scan, wherein the predetermined number is selected such that a variation of the phase information among the predetermined number of A-scans of the first B-scan is less than a predetermined degree of variation.

5. The Fourier-domain OCT imaging system according to claim 4, wherein the controller is arranged to control the FD-OCT scanner to compensate for the relative movement between the imaging target and the FD-OCT scanner during the scan by:

performing a plurality of the cross-correlation calculations to calculate a respective two-dimensional cross-correlation between each set of a plurality of sets of the predetermined number of A-scans of the first B-scan and respective A-scans of the second B-scan, the respective A-scans of the second B-scan including A-scans that are correspondingly located in the second B-scan to the predetermined number of A-scans in the set;

combining the calculated cross-correlations to determine, as the offset value, a value that is indicative of an offset between the first B-scan and the second B-scan; and controlling the FD-OCT scanner to compensate for the relative movement between the imaging target and the FD-OCT scanner by using the determined offset value that is indicative of the offset between the first B-scan and the second B-scan.

6. The Fourier-domain OCT imaging system according to claim 2, wherein the FD-OCT scanner is arranged to generate the complex OCT data by performing, as the scan, an area OCT scan of the imaging target to acquire samples having complex values that are indicative of the optical property of the imaging target at respective scan locations that are distributed three-dimensionally in the imaging target, and the controller is arranged to perform the cross-correlation calculation by acquiring, as the first set of samples, a set of samples comprising samples which have been acquired by the FD-OCT scanner scanning the imaging target along the first scan line as at least a part of the area OCT scan, wherein the second scan line crosses the first scan line.

7. The Fourier-domain OCT imaging system according to claim 6, wherein the first scan line is one of a plurality of parallel scan lines on the imaging target, the FD-OCT scanner being arranged to perform the area OCT scan by scanning the imaging target along the plurality of parallel scan lines, and to generate an OCT C-scan as the complex OCT data, based on the area OCT scan.

8. The Fourier-domain OCT imaging system according to claim 7, wherein the controller is arranged to perform the cross-correlation calculation by acquiring, as the first set of samples, the complex OCT data of the C-scan.

9. The Fourier-domain OCT imaging system according to claim 6, wherein the first scan line extends along two dimensions on the imaging target.

10. The Fourier-domain OCT imaging system according to claim 9, wherein the first scan line defines one of a square, a triangle, a diamond, a circle, an ellipse, a spiral, a square spiral, a Lissajous figure, an epitrochoid, and a hypotrochoid on the imaging target.

11. The Fourier-domain OCT imaging system according to claim 6, wherein the first scan line and the second scan line are different respective parts of a single scan line that extends along two dimensions on the imaging target and crosses itself.

12. The Fourier-domain OCT imaging system according to claim 11, wherein the single scan line defines one of a Lissajous figure, an epitrochoid, and a hypotrochoid on the imaging target.

13. A computer-implemented method of controlling a Fourier-domain optical coherence tomography, FD-OCT, scanner, which is generating complex OCT data by performing a scan of an imaging target to acquire samples whose complex values are indicative of an optical property of the imaging target at respective scan locations in the imaging target, to compensate for a relative movement between the imaging target and the FD-OCT scanner during the scan, the method comprising:

performing a cross-correlation calculation that uses phase information of the acquired samples; and controlling a scanning system of the FD-OCT scanner, based on the cross-correlation calculation, to compensate for the relative movement between the imaging target and the FD-OCT scanner during the scan, wherein the FD-OCT scanner comprises the scanning system and the scanning system is arranged to perform a scan of a light beam across the imaging target and to collect light scattered by the imaging target during the scan.

14. The computer-implemented method according to claim 13, wherein:

the cross-correlation calculation is performed by:

acquiring a first set of the samples, the samples of the first set comprising samples that have been acquired by the FD-OCT scanner scanning the imaging target along a first scan line on the imaging target;

acquiring a second set of the samples, the samples of the second set comprising samples that have been acquired by the FD-OCT scanner scanning the imaging target along a second scan line on the imaging target, wherein the second scan line at least partially overlaps the first scan line; and performing the cross-correlation calculation to calculate a two-dimensional cross-correlation between a third set of samples comprising at least some samples of the first set of samples, and a fourth set of samples comprising at least some samples of the second set of samples, at least some samples of the third set of samples and at least some samples of the fourth set of samples having been acquired from a common region of the imaging target at which the first scan line and the second scan line overlap, the cross-correlation calculation being based on phase information in the third set of samples and phase information in the fourth set of samples, and the FD-OCT scanner is controlled to compensate for the relative movement between the imaging target and the FD-OCT scanner during the scan by:

registering the first set of samples and the second set of samples with respect to each other using the calculated cross-correlation to determine a value of an offset indicator that is indicative of an offset between scan locations of the first set of samples and scan locations of the second set of samples; and using the determined value of the offset indicator to control the FD-OCT scanner, during the scan, to compensate for a relative movement between the imaging target and the FD-OCT scanner that occurred between the acquisition of the first set of samples and the acquisition of the second set of samples by the FD-OCT scanner.

15. A non-transitory computer-readable storage medium comprising computer-readable instructions, which, when executed by a processor that is controlling a Fourier-domain optical coherence tomography, FD-OCT, scanner to generate complex OCT data by performing a scan of an imaging target to acquire samples whose complex values are indicative of an optical property of the imaging target at respective scan locations in the imaging target, cause the processor to control the FD-OCT scanner to compensate for a relative movement between the imaging target and the FD-OCT scanner during the scan, by performing a method comprising:

performing a cross-correlation calculation that uses phase information of the acquired samples; and controlling a scanning system of the FD-OCT scanner, based on the cross-correlation calculation, to compensate for the relative movement between the imaging target and the FD-OCT scanner during the scan, wherein the FD-OCT scanner comprises the scanning system and the scanning system is arranged to perform a scan of a light beam across the imaging target and to collect light scattered by the imaging target during the scan.

16. The non-transitory computer-readable storage medium of claim 15, wherein:

the cross-correlation calculation is performed by:

acquiring a first set of the samples, the samples of the first set comprising samples that have been acquired by the FD-OCT scanner scanning the imaging target along a first scan line on the imaging target;

acquiring a second set of the samples, the samples of the second set comprising samples that have been acquired by the FD-OCT scanner scanning the imaging target along a second scan line on the imaging target, wherein the second scan line at least partially overlaps the first scan line; and performing the cross-correlation calculation to calculate a two-dimensional cross-correlation between a third set of samples comprising at least some samples of the first set of samples, and a fourth set of samples comprising at least some samples of the second set of samples, at least some samples of the third set of samples and at least some samples of the fourth set of samples having been acquired from a common region of the imaging target at which the first scan line and the second scan line overlap, the cross-correlation calculation being based on phase information in the third set of samples and phase information in the fourth set of samples, and the FD-OCT scanner is controlled to compensate for the relative movement between the imaging target and the FD-OCT scanner during the scan by:

registering the first set of samples and the second set of samples with respect to each other using the calculated cross-correlation to determine a value of an offset indicator that is indicative of an offset between scan locations of the first set of samples and scan locations of the second set of samples; and using the determined value of the offset indicator to control the FD-OCT scanner, during the scan, to compensate for a relative movement between the imaging target and the FD-OCT scanner that occurred between the acquisition of the first set of samples and the acquisition of the second set of samples by the FD-OCT scanner.

17. The Fourier-domain OCT imaging system according to claim 1, wherein:

the cross-correlation calculation is performed during the scan, after acquiring a first set of samples and a second set of samples, the cross-correlation calculation comprising:

calculating a cross-correlation between phase information in the first set of samples and phase information in the second set of samples; and the controller controls the scanning system, after acquiring the first set of samples and the second set of samples, to acquire a third set of the samples, by:

using the calculated cross-correlation for the first set and the second set to determine an offset between the first set of samples and the second set of samples; and acquiring, during the scan, the third set of samples according to the determined offset, thereby compensating for a relative movement between the imaging target and the FD-OCT scanner that occurred prior to acquisition of the third set of samples by the FD-OCT scanner.

18. The computer-implemented method according to claim 13, wherein:

the cross-correlation calculation is performed during the scan, after acquiring a first set of samples and a second set of samples, the cross-correlation calculation comprising:

calculating a cross-correlation between phase information in the first set of samples and phase information in the second set of samples; and the controlling is performed, after acquiring the first set of samples and the second set of samples, to acquire a third set of the samples, by:

using the calculated cross-correlation for the first set and the second set to determine an offset between the first set of samples and the second set of samples; and acquiring, during the scan, the third set of samples according to the determined offset, thereby compensating for a relative movement between the imaging target and the FD-OCT scanner that occurred prior to acquisition of the third set of samples by the FD-OCT scanner.

19. The non-transitory computer-readable storage medium of claim 15, wherein:

the cross-correlation calculation is performed during the scan, after acquiring a first set of samples and a second set of samples, the cross-correlation calculation comprising:

calculating a cross-correlation between phase information in the first set of samples and phase information in the second set of samples; and the controlling is performed, after acquiring the first set of samples and the second set of samples, to acquire a third set of the samples, by:

using the calculated cross-correlation for the first set and the second set to determine an offset between the first set of samples and the second set of samples; and acquiring, during the scan, the third set of samples according to the determined offset, thereby compensating for a relative movement between the imaging target and the FD-OCT scanner that occurred prior to acquisition of the third set of samples by the FD-OCT scanner.

20. The Fourier-domain OCT imaging system according to claim 1, wherein the relative movement compensated for by the scanning system occurred prior to acquisition of additional samples during the scan, thereby acquiring the additional samples according to the relative movement compensation.

* * * * *